(12) United States Patent
Nakamura

(10) Patent No.: US 11,317,790 B2
(45) Date of Patent: May 3, 2022

(54) FLEXIBLE TUBE INSERTION DEVICE, INSERTION CONTROL DEVICE, AND INSERTION METHOD

(71) Applicant: OLYMPUS CORPORATION, Tokyo (JP)

(72) Inventor: Shuji Nakamura, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 211 days.

(21) Appl. No.: 16/686,313

(22) Filed: Nov. 18, 2019

(65) Prior Publication Data

US 2020/0100653 A1 Apr. 2, 2020

Related U.S. Application Data

(63) Continuation of application No. PCT/JP2017/019384, filed on May 24, 2017.

(51) Int. Cl.
*A61B 1/005* (2006.01)
*A61B 1/00* (2006.01)

(52) U.S. Cl.
CPC ........ *A61B 1/0055* (2013.01); *A61B 1/00006* (2013.01); *A61B 1/00055* (2013.01); *A61B 1/00078* (2013.01)

(58) Field of Classification Search
CPC ..... A61B 1/0055; A61B 1/005; A61B 1/0051; A61B 1/0053; A61B 1/0056;
(Continued)

(56) References Cited

U.S. PATENT DOCUMENTS 10,349,819 B2 * 7/2019 Ikeda ................. A61B 1/00
10,517,461 B2 * 12/2019 Nakamura ........... A61B 1/008
(Continued)

FOREIGN PATENT DOCUMENTS

JP 2006-218232 A 8/2006
JP 2016-007434 A 1/2016
(Continued)

OTHER PUBLICATIONS

International Search Report dated Aug. 22, 2017 issued in PCT/JP2017/019384.
(Continued)

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

A flexible tube insertion device includes a flexible tube section, at least one variable stiffness unit, at least one state detector, and a stiffness controller. The flexible tube section is segmented along an axial direction into segments and configured to be inserted into an insertion target. The variable stiffness unit is configured to vary bending stiffness of the flexible tube section in units at least one segment. The state detector is configured to detect information relating to shape information of the flexible tube section. The stiffness controller is configured to cause the variable stiffness unit to reduce bending stiffness of a portion of the flexible tube section including a place where the flexible tube section is easy to bend in units of at least one segment based on the shape information.

17 Claims, 22 Drawing Sheets

(58) Field of Classification Search
CPC ... A61B 1/0057; A61B 1/00078; A61B 1/009; A61B 1/00006; A61B 1/00071; A61B 1/012; A61B 1/00105
USPC .......................................... 600/143–146, 152
See application file for complete search history.

(56) References Cited

U.S. PATENT DOCUMENTS

| | | | |
|---|---|---|---|
| 10,959,604 B2* | 3/2021 | Ikeda ................. | A61B 1/00066 |
| 2007/0149852 A1* | 6/2007 | Noguchi ............ | A61B 1/00147 600/144 |
| 2007/0270649 A1* | 11/2007 | Long .................. | A61B 1/0053 600/144 |

FOREIGN PATENT DOCUMENTS

| WO | WO 2006/028019 A1 | 3/2006 |
|---|---|---|
| WO | WO 2015/198761 A1 | 12/2015 |

OTHER PUBLICATIONS

English translation of International Preliminary Report on Patentability dated Dec. 5, 2019, together with the Written Opinion received in related International Application No. PCT/JP2017/019384.

\* cited by examiner

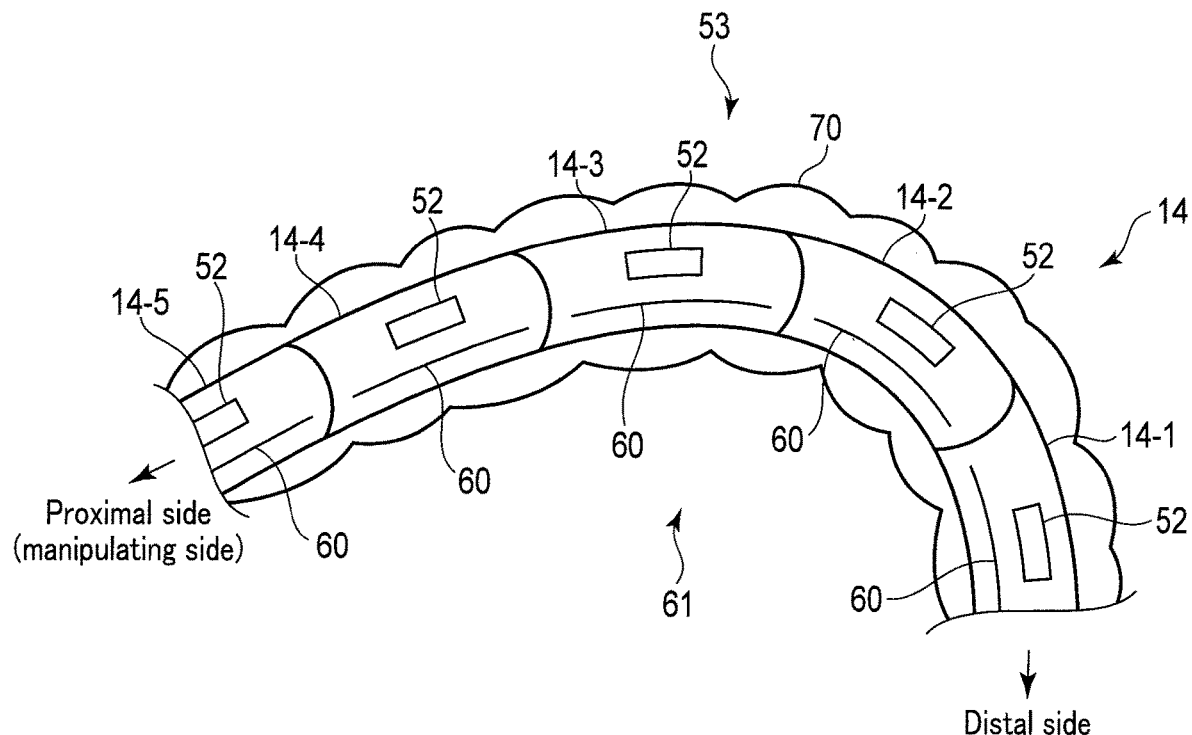
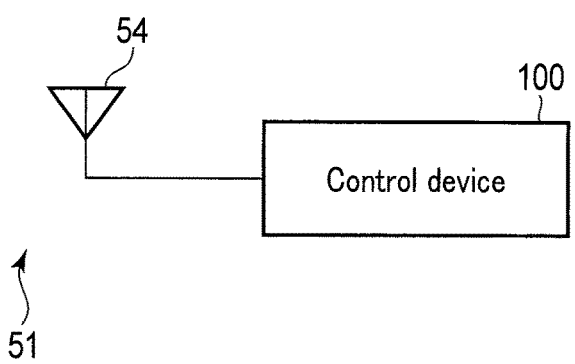
F I G. 2

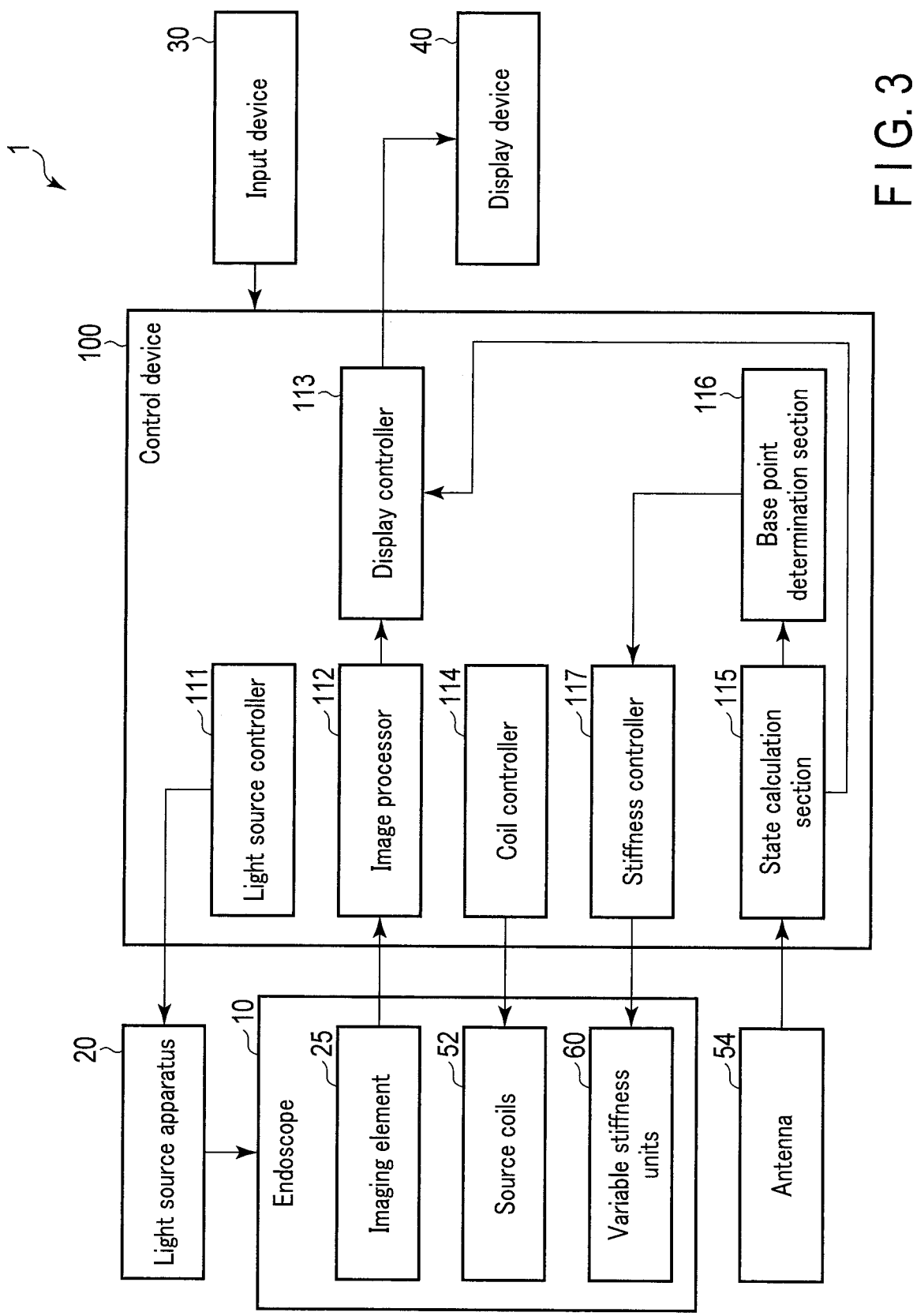
F I G. 3

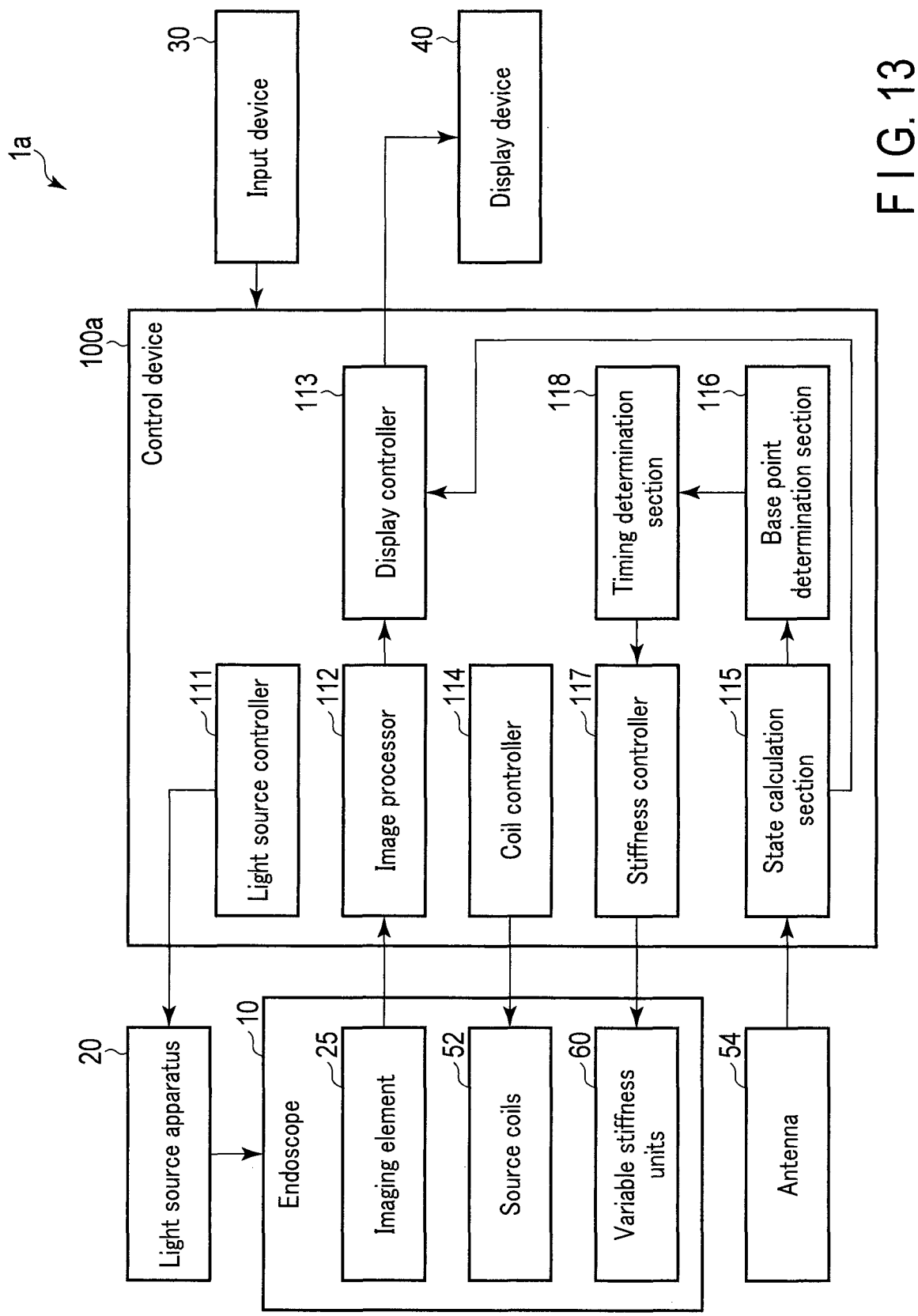
F I G. 13

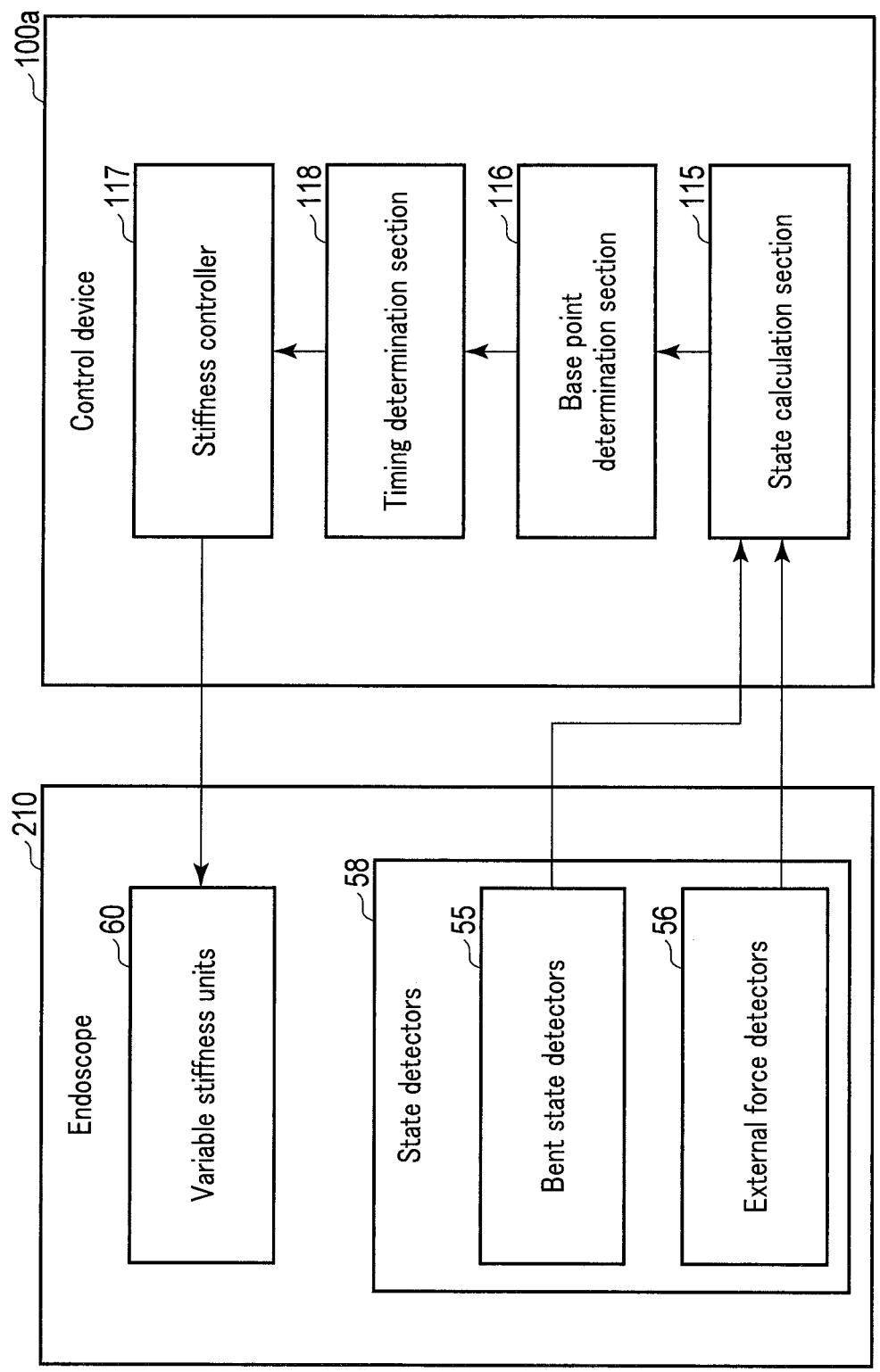
F I G. 20

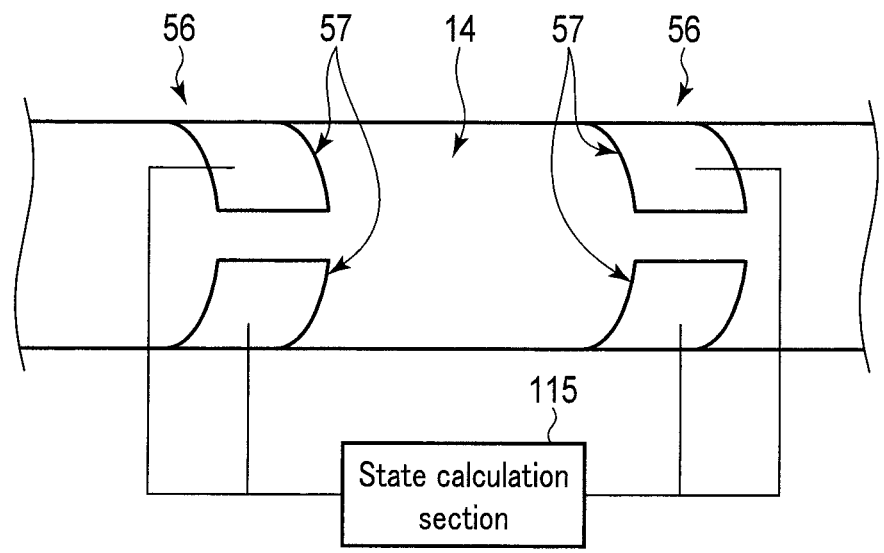
F I G. 21
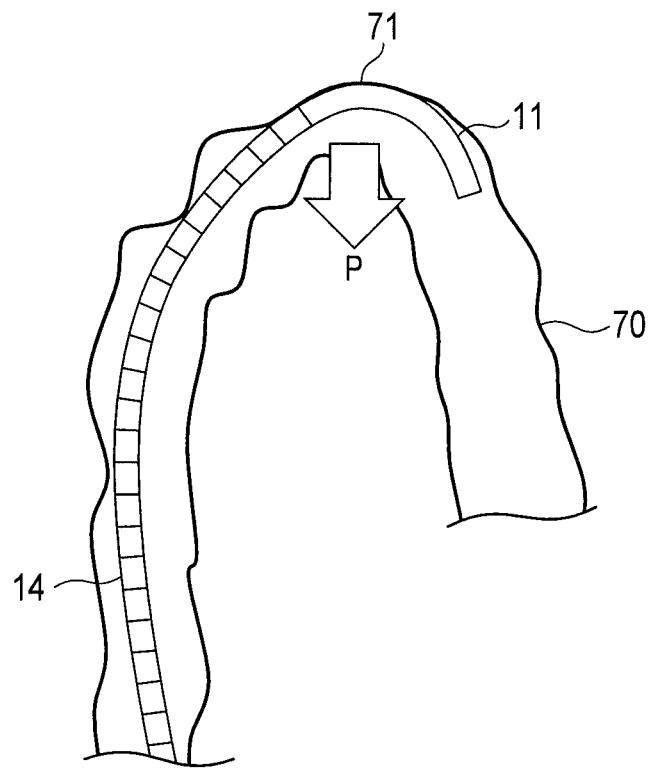
F I G. 22

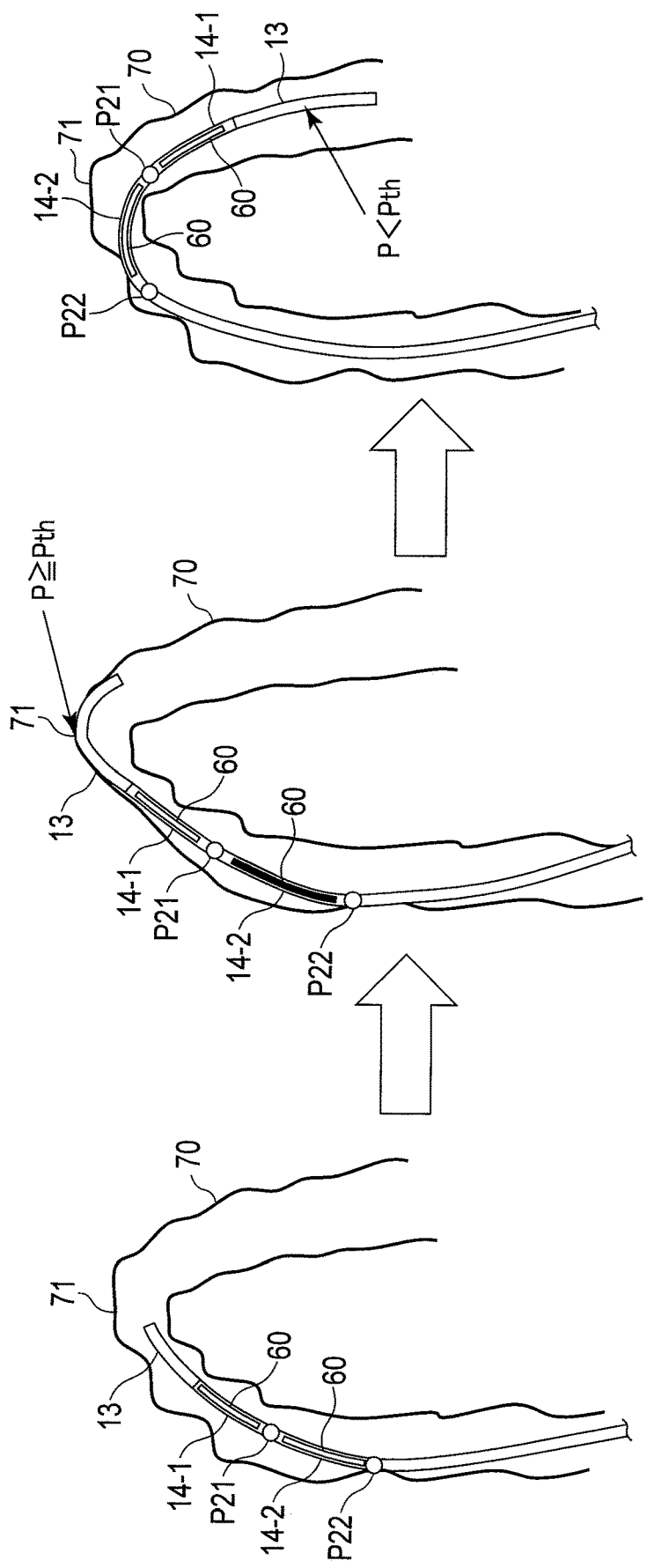
F I G. 25

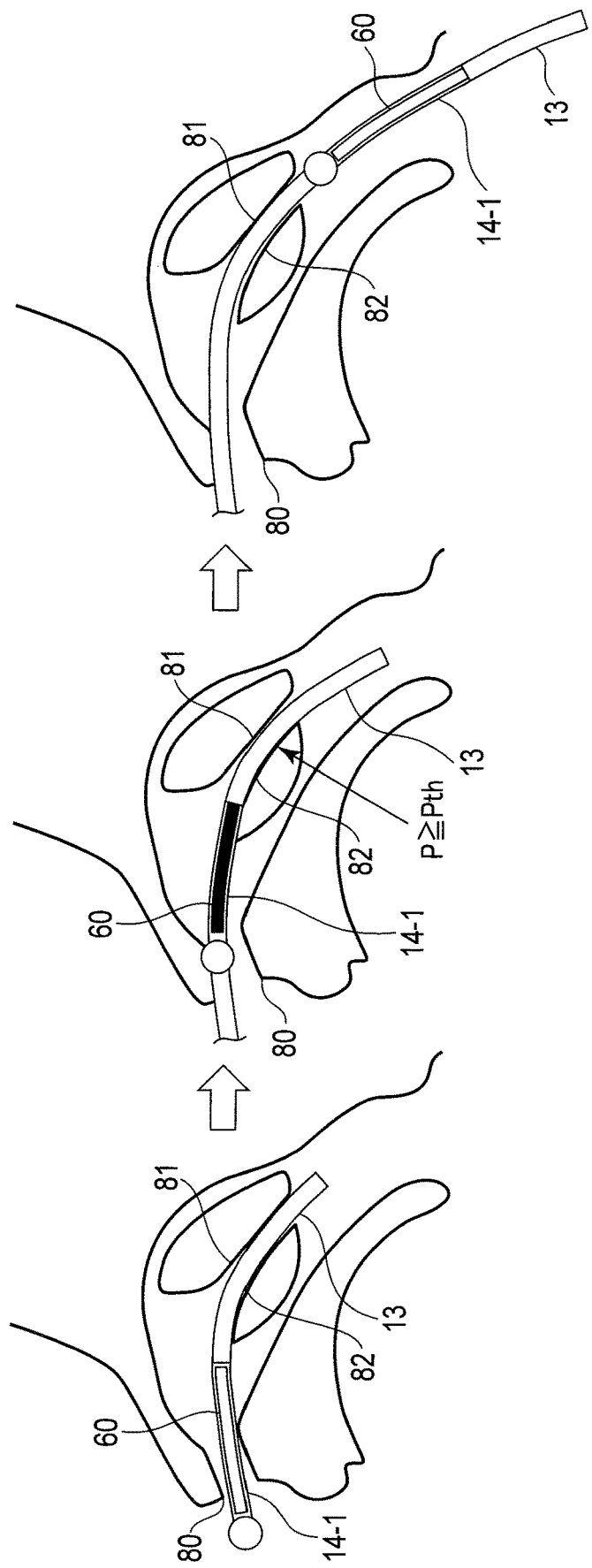
F I G. 26

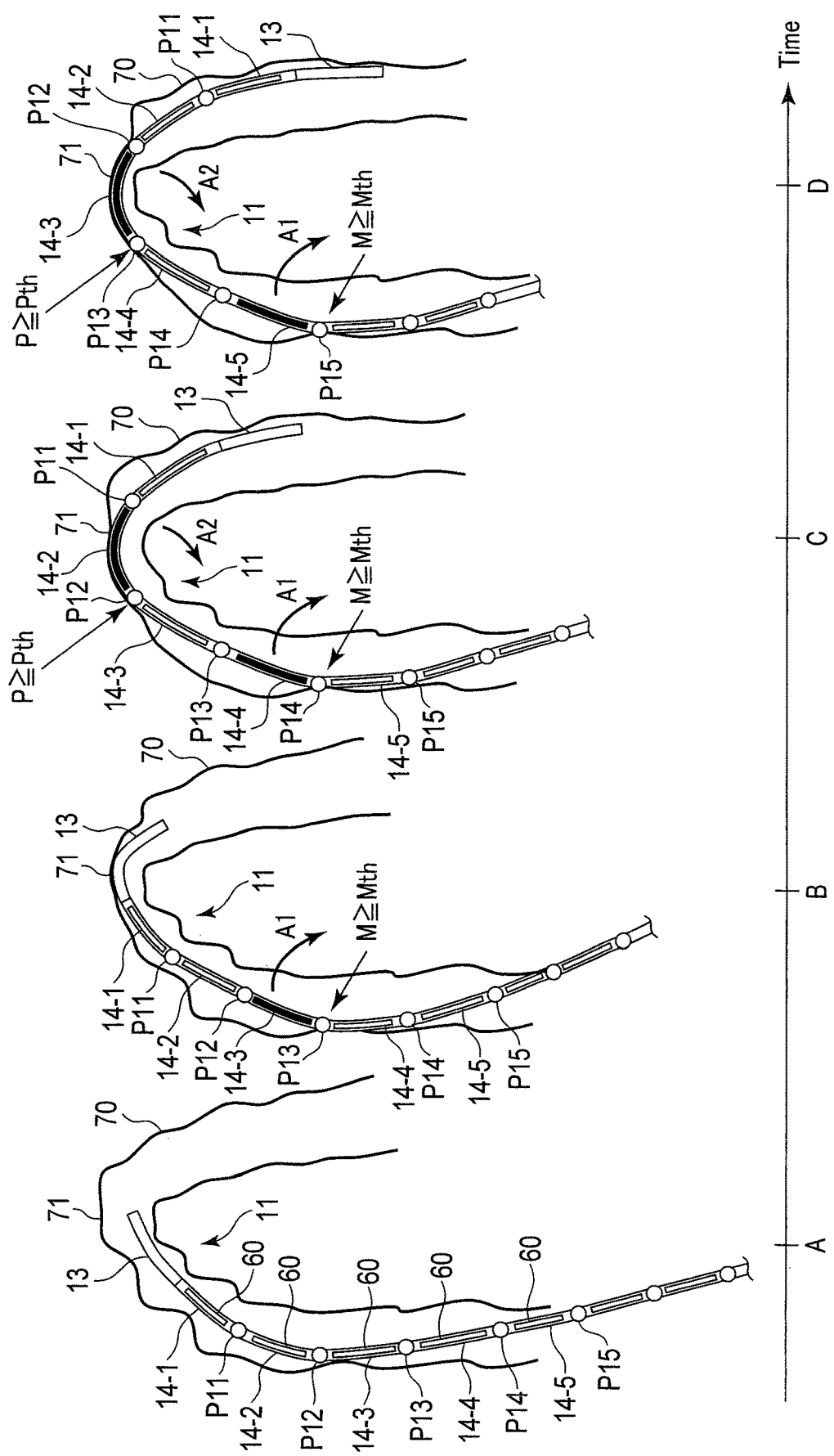
F I G. 28

FLEXIBLE TUBE INSERTION DEVICE, INSERTION CONTROL DEVICE, AND INSERTION METHOD

CROSS-REFERENCE TO RELATED APPLICATIONS

This application is a Continuation Application of PCT Application No. PCT/JP2017/019384, filed May 24, 2017, the entire contents of which are incorporated herein by reference.

BACKGROUND OF THE INVENTION

1. Field of the Invention

The present invention relates to a flexible tube insertion device having a flexible tube section to be inserted into an insertion target, an insertion control device, and an insertion method.

2. Description of the Related Art

In order to improve the insertability of the insertion section (flexible tube section) of a flexible tube insertion device such as an endoscope apparatus, the technique of varying the bending stiffness of part of the insertion section is widely known.

For example, Jpn. Pat. Appln. KOKAI Publication No. 2006-218232 discloses an endoscope apparatus having an insertion section, which includes a bendable section, a first flexible tube section, and a second flexible tube section, in this order from the distal end. The first flexible tube section constitutes a passively bendable section that is passively bent under a predetermined amount of force received from a flexure of an insertion target when the first flexible tube section is inserted into the insertion target and passes through the flexure. In such an endoscope apparatus, since the passively bendable section is bent when passing through the flexure, only light load is applied to the flexure, enhancing the insertability.

Jpn. Pat. Appln. KOKAI Publication No. 2016-7434 discloses an endoscope apparatus in which the insertion section is divided into segments in the longitudinal direction, the shape of each segment is detected, and the bending stiffness of each segment is varied according to the detected bent shape, so that the insertability is improved.

BRIEF SUMMARY OF THE INVENTION

An aspect of the present invention is directed to a flexible tube insertion device. The flexible tube insertion device includes a flexible tube section segmented along an axial direction into segments and configured to be inserted into an insertion target, at least one variable stiffness unit configured to vary bending stiffness of the flexible tube section in units of at least one segment, at least one state detector configured to detect information relating to shape information of the flexible tube section and a stiffness controller configured to cause the at least one variable stiffness unit to reduce bending stiffness of a portion of the flexible tube section including a place where the flexible tube section is easy to bend in units of at least one segment based on the shape information.

Another aspect of the present invention is directed to an insertion control device of a flexible tube section. The flexible tube section is segmented along an axial direction into segments and configured to be inserted into an insertion target. The insertion control device includes a base point determination section configured to detect a place where the flexible tube section is easy to bend to determine the place as a base point of varying bending stiffness of the flexible tube section, based on shape information obtained by at least one state detector configured to detect the shape information of the flexible tube section, and a stiffness controller configured to cause at least one variable stiffness unit to vary the bending stiffness of a portion of the flexible tube section including the place where the flexible tube section is easy to bend in units of at least one segment.

Still another aspect of the present invention is directed to an insertion method of a flexible tube section into an examination target. The flexible tube section is segmented along an axial direction into segments. The method includes inserting the flexible tube section into the examination target, and controlling stiffness of the flexible tube section so that the stiffness of a segment including a place where the flexible tube section is easy to bend is reduced.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a diagram showing an example of a flexible tube section of the endoscope apparatus including a bent shape detection device.

FIG. 3 is a block diagram showing an exemplary endoscope apparatus according to the first embodiment.

FIG. 13 is a block diagram showing an example of the endoscope apparatus according to the second embodiment.

FIG. 20 is a block diagram showing part of the endoscope and the control device of the endoscope apparatus according to the third embodiment.

FIG. 21 is a schematic diagram showing an exemplary arrangement of external force detectors.

FIG. 22 is a diagram illustrating an exemplary state of the insertion section in contact with a flexure.

FIG. 25 shows an example of the bending stiffness control of the flexible tube section.

FIG. 26 shows an example of the bending stiffness control of the flexible tube section.

FIG. 28 shows an example of the bending stiffness control of the flexible tube section.

DETAILED DESCRIPTION OF THE INVENTION

Embodiments of the present invention will be described below, with reference to the drawings. Hereinafter, an endoscope apparatus will be discussed as an example of the flexible tube insertion device of the present invention.

First Embodiment

Figure 1:
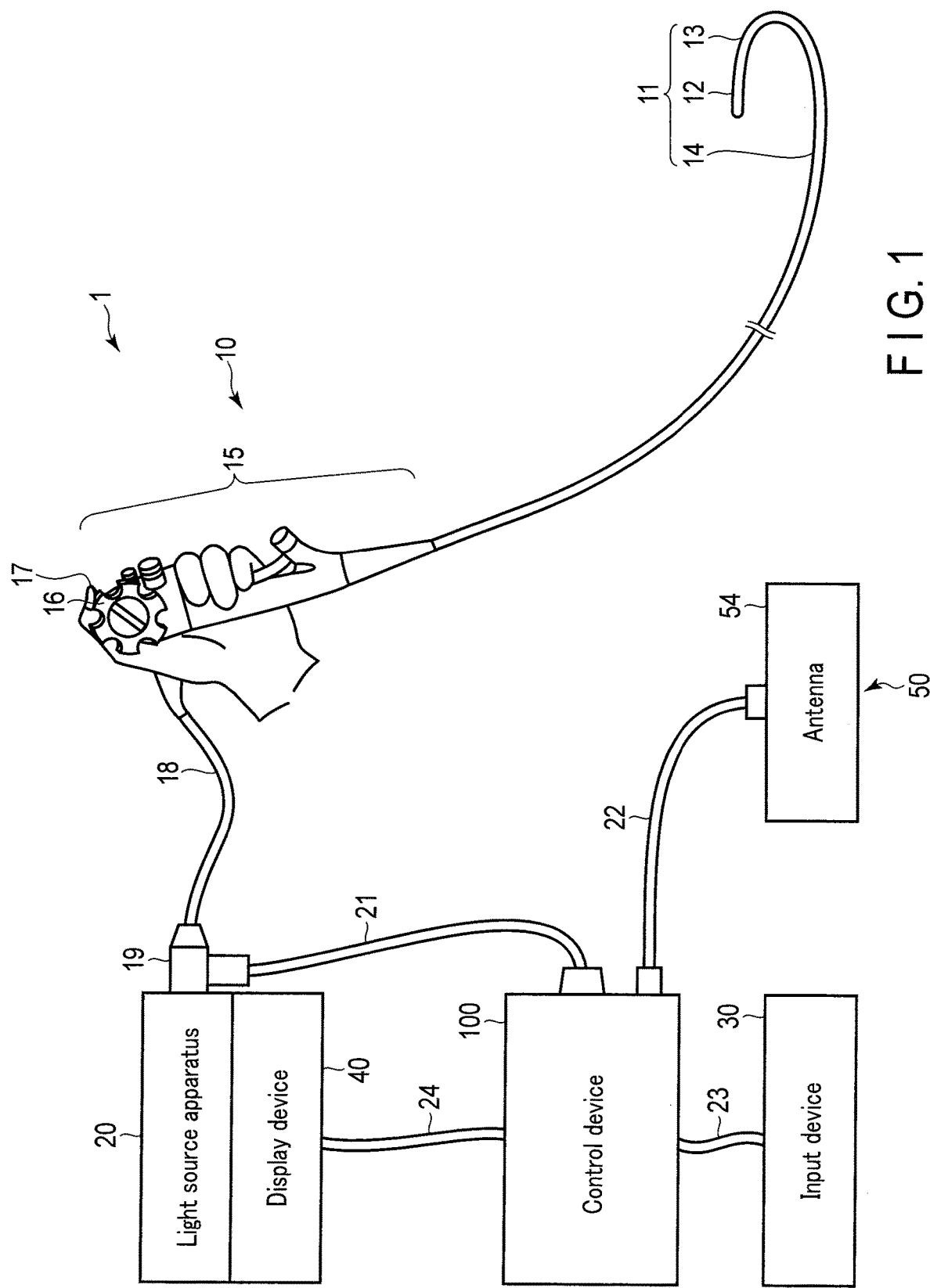
FIG. 1 is a diagram schematically showing an example of an endoscope apparatus according to the first embodiment.

The first embodiment of the present invention will be described with reference to FIGS. 1 to 12. FIG. 1 is a diagram schematically showing an example of an endoscope apparatus 1. The endoscope apparatus 1 includes an endoscope 10, a light source apparatus 20, an input device 30, a display device 40, and a control device 100.

The endoscope 10 includes a tubular insertion section 11 to be inserted into an insertion target, and a control section 15 provided at the proximal end of the insertion section 11. The insertion section 11 includes a distal end hard section 12, a bendable section 13, and a flexible tube section 14 arranged in this order from the distal end to the proximal end. The distal end hard section 12 incorporates therein an optical system for illumination and an optical system for observation (not shown), as well as an imaging element 25 shown in FIG. 3. The bendable section 13 is a portion that is bent in accordance with the operation of the control section 15. The bendable section 13 is connected to the distal end of the flexible tube section 14. The flexible tube section 14 is a flexible, elongated tubular portion. The control section 15 includes an angle knob 16, which allows the bendable section 13 to be bent in a desired direction when a surgeon manipulates the angle knob 16. In other words, the bendable section 13 can actively change its bent shape. The control section 15 is further provided with one or more switches 17. The functions, such as freezing and recording endoscope images, switching focus, etc., are assigned to these switches 17 by settings of the control device 100.

The endoscope apparatus 1 includes a state detection device 50. The state detection device 50 according to the present embodiment is configured to detect information (state information) regarding the state of the flexible tube section 14. The state of the flexible tube section 14 indicates the bent shape of the flexible tube section, for example. The state information is used for calculation of the bent shape (bent angle, bent amount, curvature or curvature radius, etc.) of the flexible tube section 14, for example. As an example of the state detection device 50, a bent shape detection device 51 composed of a magnetic sensor is illustrated in FIG. 2.

FIG. 2 is a schematic diagram showing an example of the flexible tube section 14 of the endoscope apparatus 1 that includes a bent shape detection device 51 of a magnetic sensor type. The flexible tube section 14 illustrated in FIG. 2 is inserted in a large intestine 70, which is a curvy insertion target. The bent shape detection device 51 includes a source coil array 53, composed of source coils 52, for detection of the bent state of the flexible tube section 14. The source coil 52 is a magnetic field generating element that generates a magnetic field.

Each of the source coils 52 in the source coil array 53 is arranged at intervals in the longitudinal direction (axial direction) of the flexible tube section 14. For the sake of simplicity, it is assumed that the flexible tube section 14 is formed of one or more segments in the axial direction (virtual units that are obtained by equally dividing the flexible tube section 14 in the longitudinal direction). That is, it is assumed that the flexible tube section 14 is divided into segments along the axial direction from the distal end to the proximal end. For example, FIG. 2 shows five segments 14-1, 14-2, 14-3, 14-4, and 14-5 aligned along the axial direction from the distal end to the proximal end; each of the segments is provided with one source coil 52. The arrangement of the source coils 52 is not limited to the above, and the source coils may be arranged only in part of the segments.

The bent shape detection device 51 includes an antenna 54 for detecting the magnetic field generated by the source coil 52. The antenna 54 is provided separately from the endoscope 10, and is positioned around the insertion target into which the endoscope 10 is inserted. The antenna 54 is connected to the control device 100.

Although FIG. 2 shows a configuration in which the source coils 52 are preinstalled in the flexible tube section 14, a probe incorporating source coils may be inserted in a channel extending in the longitudinal direction in the insertion section 11.

By referring to FIG. 1 again, the light source apparatus 20 is connected to the endoscope 10 through a cable connector 19 at the end of a universal cable 18 extending from the control section 15. The universal cable 18 includes a light guide connected to the above-mentioned optical system for illumination, a transmission cable connected to the imaging element 25, and the like. The light source apparatus 20 includes general light emitting elements such as laser diodes (LD) and light emitting diodes (LED). The light source apparatus 20 supplies illumination light that will be emitted from the illumination window of the distal end hard section 12 through the light guide.

FIG. 3 is a block diagram showing an example of the endoscope apparatus 1 according to the first embodiment. The control device 100 includes a light source controller 111, an image processor 112, a display controller 113, a coil controller 114, a state calculation section 115, a base point determination section 116, and a stiffness controller 117. As shown in FIG. 1, the control device 100 is connected to the endoscope 10 and the light source apparatus 20 through the cable connector 19 and cable 21. The control device 100 is also connected to the antenna 54 through the cable 22.

Each of the above-described functional elements of the control device 100 may be composed of a processor such as a CPU. In this case, various programs for causing the processor to function as these elements are prepared in an internal memory or an external memory (not shown), and the processor executes the programs to implement functions of the elements of the control device 100. Alternatively, each of the elements of the control device 100 may be composed of a hardware circuit including an application specific integrated circuit (ASIC), a field-programmable gate array (FPGA), and the like.

The above-described elements of the control device 100, in particular, the state calculation section 115, the base point determination section 116, and the stiffness controller 117, may be provided in a control device separately from the control device 100. For example, the state calculation section 115, the base point determination section 116, and the stiffness controller 117 may be included in a control device separately from the endoscopic video image processor, which includes the light source controller 111 and the image processor 112. Alternatively, the state calculation section 115, the base point determination section 116, and the stiffness controller 117 may be included in different control devices. That is, the processor or hardware circuits that function as the above-mentioned elements of the control device 100, in particular, the state calculation section 115, base point determination section 116, and stiffness controller 117, may be provided in a single housing or in multiple housings, as long as the functions of these elements can be implemented.

The light source controller 111 performs dimming control of the illumination light of the light source apparatus 20. The image processor 112 converts the electric signal obtained by converting the light from the target by the imaging element 25 of the endoscope 10, into a video signal. The display controller 113 controls the operation of the display device 40.

The coil controller 114 includes a coil output section that outputs a voltage to be applied to each of the source coils 52 of the source coil array 53, and controls this voltage to be applied to the source coils 52 by the coil output section.

The state calculation section 115 calculates the coordinates of the position of each source coil 52 based on the detection signal of the magnetic field of each source coil 52 received by the antenna 54. That is, the state calculation section 115 calculates the bent shape information (shape information) of the flexible tube section 14, based on the state information acquired from the source coils 52 (state detectors) and the antenna 54. The state calculation section 115 includes a receiver that receives a detection signal from the antenna 54.

The base point determination section 116 determines the base point of the variation in bending stiffness in the variable stiffness units 60 that are provided in respective segments of the flexible tube section 14, based on the shape information calculated by the state calculation section 115. The stiffness controller 117 includes a variable stiffness output section that outputs a voltage to be applied to the variable stiffness unit 60, which will be described later, and controls the voltage applied to the variable stiffness unit 60 by the variable stiffness output section.

According to the present embodiment, the source coils 52 of the source coil array 53, the antenna 54, and the coil controller 114 and the state calculation section 115 of the control device 100 constitute a bent shape detection device 51. In order to support the insertion of the insertion section 11 of the endoscope 10, the bent shape detection device 51, as the state detection device 50, receives the magnetic fields generated by the source coils 52 of the source coil array 53 with the antenna 54 to detect the state information of the flexible tube section 14, and calculates the shape information of the flexible tube section 14 based on the state information at the state calculation section 115.

The bent shape detection device 51 as the state detection device 50 is not limited to the above. The bent shape detection device needs to be configured to detect the bent shape of the flexible tube section 14 (bent angle, bent amount, curvature or curvature radius, etc.). For example, the curved bent shape detection device can be composed of any one of or a combination of sensing that utilizes changes in a quantity or an optical property of light that propagates through a light guide such as an optical fiber (fiber sensor), sensing that utilizes electromagnetic waves (electromagnetic sensor), sensing that utilizes ultrasonic waves (ultrasonic sensor), sensing that utilizes distortion (distortion sensor), and sensing that utilizes an X-ray absorbing material.

Next, the variable stiffness unit 60 will be described. As shown in FIG. 2, the flexible tube section 14 is provided with a variable stiffness unit array 61 that includes at least one variable stiffness unit (variable stiffness actuator) 60. The variable stiffness units 60 vary the bending stiffness (hardness) of the flexible tube section 14 in units of segments, targeting the corresponding segments in which they are arranged. The variable stiffness units 60 can vary the bending stiffness of the segments in which they are arranged, for each segment within a range of a predetermined minimum bending stiffness value to a maximum bending stiffness value.

Figure 4:
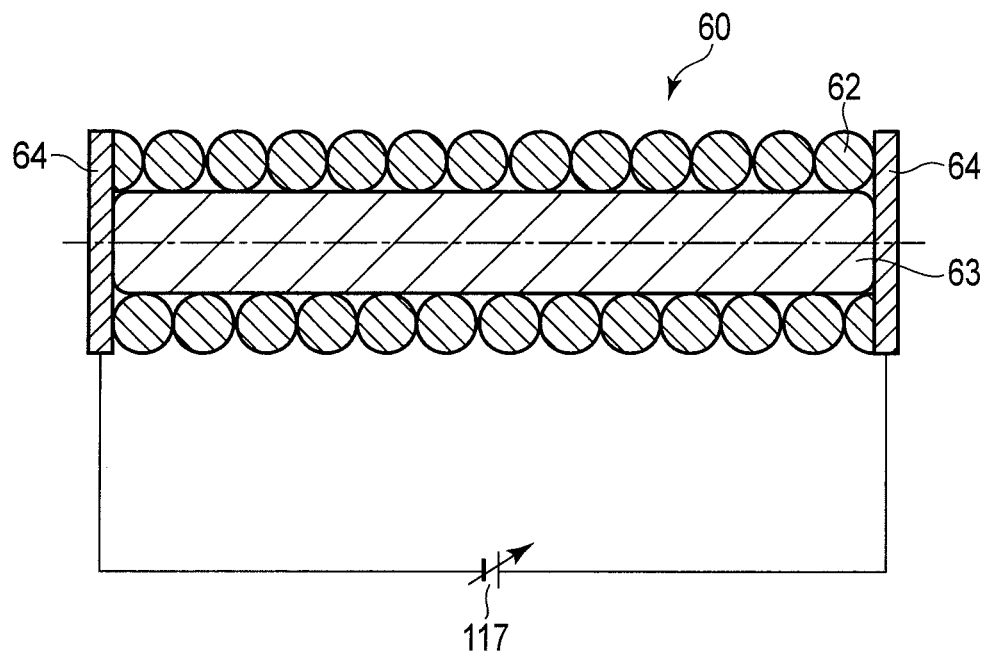
FIG. 4 is a diagram schematically showing an exemplary variable stiffness unit.

FIG. 4 is a schematic diagram showing an example of the variable stiffness unit 60. The variable stiffness unit 60 includes a coil pipe 62 made of a metal wire, an electroactive polymer artificial muscle (EPAM) 63 bundled in the coil pipe 62, and electrodes 64 provided at the both ends of the coil pipe 62. The voltage output from the stiffness controller 117 is applied across the EPAM 63 inside the coil pipe 62 through the electrodes 64. The EPAM 63 is an actuator that expands and contracts under application of a voltage, so as to vary the hardness. Each of the variable stiffness units 60 is incorporated in the flexible tube section 14 such that the central axis of the coil pipe 62 is coincident with or parallel to the central axis of the flexible tube section 14. The EPAM 63 of each variable stiffness unit 60 has a stiffness greater than that of the member that forms the flexible tube section 14 (e.g., fluororesin).

Figure 5:
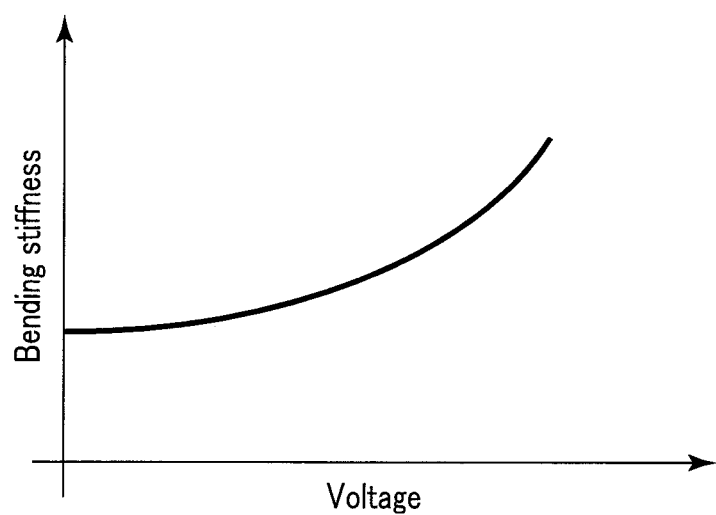
FIG. 5 is a diagram showing an example of the voltage versus bending stiffness of the variable stiffness unit.

When the stiffness controller 117 outputs a voltage from its variable stiffness output section, the voltage is applied between the electrodes 64 of the variable stiffness unit 60 (across the EPAM 63). When the voltage is applied, the EPAM 63 tends to increase its diameter about the central axis of the coil pipe 62. With the EPAM 63 bundled by the coil pipe 62, however, the increase of the diameter is hampered. As a result, the variable stiffness unit 60 exhibits a higher bending stiffness value as the applied voltage value increases, as indicated in FIG. 5. That is, in accordance with the variation in the hardness of the variable stiffness unit 60, the bending stiffness of the flexible tube section 14 incorporating the variable stiffness unit 60 also varies.

As discussed above, the endoscope apparatus 1 has a variable stiffness function to vary the bending stiffness of the flexible tube section 14 by the stiffness controller 117 applying a voltage from its variable stiffness output section to the variable stiffness units 60. The stiffness controller 117 individually controls the voltages applied from the variable stiffness output section to the variable stiffness units 60, so that the bending stiffness (hardness) of the segments of the flexible tube section 14 is independently varied. This allows for the bending stiffness values to be set differently for individual segments of the flexible tube section 14.

The input device 30 is a general input device such as a keyboard. The input device 30 is connected to the control device 100 through the cable 23. Various commands for operating the endoscope apparatus 1 are input through the input device 30. The input device 30 may be an operation panel provided on the control device 100 or a touch panel displayed on a display screen.

The display device 40 is a commonly used monitor such as a liquid crystal display. The display device 40 is connected to the control device 100 through the cable 24. The display device 40 displays an endoscopic observation image according to a video signal transmitted from the image processor 112 of the control device 100. The display device 40 may also display information regarding the state of the flexible tube section 14 based on the coordinates of the position of each source coil 52, which are calculated by the state calculation section 115 of the control device 100. The display device that displays an endoscopic observation image may be a device the same as or different from the display device that displays the information regarding the state of the flexible tube section 14.

Next, the operation of the endoscope apparatus 1 will be described. In the following example, it is assumed that the endoscope 10 is a large intestine endoscope and the insertion target is a large intestine. At the beginning of the insertion, the flexible tube section 14 exhibits a predetermined bending stiffness initial value (hardness), where the hardness is less than the maximum bending stiffness value of the variable stiffness unit 60. That is, the segments of the flexible tube section 14 may become more flexible after insertion than at the beginning of the insertion.

The insertion section 11 of the endoscope 10 is inserted into the large intestine (through the anus into the rectum and colon) by the surgeon. The insertion section 11 passes through the intestine tract, following the flexures of the intestine tract. The endoscope 10 converts the light from the target in the intestine tract into an electric signal by the imaging element 25 in the distal end hard section 12. The electric signal is then transmitted to the control device 100. The image processor 112 of the control device 100 receives the electric signal and converts the received electric signal into a video signal. Thereafter, the display controller 113 of the control device 100 displays an endoscopic observation image based on the video signal on the display device 40.

During the insertion, the coil controller 114 of the control device 100 applies voltages from its coil output section to the source coils 52. As a result, the source coils 52 generate weak magnetic fields in their respective vicinity. In other words, the positional information of each source coil 52 is output from itself. The antenna 54 detects the magnetic fields generated by the source coils 52, and outputs detection signals to the state calculation section 115.

The state calculation section 115 receives the detection signals from the antenna 54 with its receiver, and calculates the bent shape (bent angle, bent amount, curvature or curvature radius, etc.) of the flexible tube section 14 based on the signals. The display controller 113 may generate a three-dimensional image corresponding to the information of the calculated bent shape to cause the display device 40 to display the image.

The base point determination section 116 acquires the shape information calculated by the state calculation section 115. Based on the acquired shape information, the base point determination section 116 determines the base point of the variation in bending stiffness, as described later. Based on the determined base point, the stiffness controller 117 varies the bending stiffness of a variable stiffness unit 60 in a portion including the base point.

As described above, in the endoscope apparatus 1, the stiffness controller 117 controls the variable stiffness units 60 to vary the bending stiffness of the flexible tube section 14, in accordance with the shape information calculated from the state information of the flexible tube section 14 that is currently inserted.

Next, the base point of the variation in bending stiffness in each segment of the flexible tube section 14 according to the present embodiment will be described with reference to FIGS. 6 to 8. According to the present embodiment, the base point determination section 116 calculates the bending moment of the flexible tube section 14 based on the shape information acquired from the state calculation section 115, and determines, as the base point of the variation in bending stiffness, a place where the flexible tube section is easy to bend, based on the calculated bending moment. The bending moment represents the force of the flexible tube section 14 resisting the bending. The flexible tube section 14 is difficult to bend where the bending moment is small, and easy to bend where the bending moment is large. That is, in the present embodiment, for example, a place where the flexible tube section is easy to bend is at a position of the flexible tube section 14 at which the value of the bending moment indicates the local maximum value or the maximum value.

Figure 6:
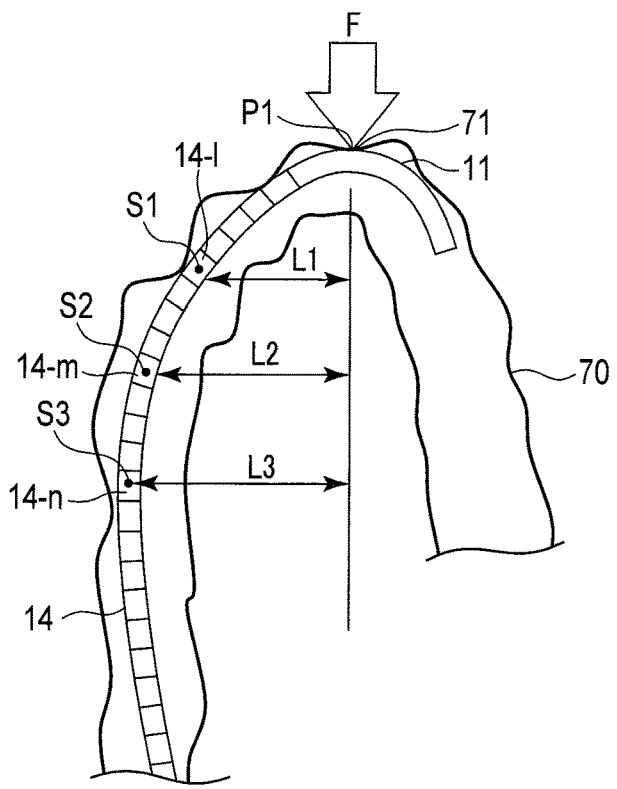
FIG. 6 is a conceptual diagram for calculation of the bending moment of the insertion section.

FIG. 6 is a schematic diagram showing the insertion state of the insertion section 11 in the large intestine 70, describing the concept of the calculation of the bending moments of the flexible tube section 14. It is assumed here that the insertion section 11 receives an external force F from the intestine wall at a contact point P1 where the insertion section 11 is in contact with the flexure 71 (e.g., the bent top of the sigmoid colon, or so-called "S-top"). As shown in FIG. 6, when the bending moments at points S1, S2, and S3 included in the segments 14-1, 14-m, and 14-n (each segment including an unillustrated variable stiffness unit 60) of the flexible tube section 14 are denoted as M1, M2, and M3, respectively, the bending moments M1, M2, and M3 are represented as:

$$M1 = F \times L1,$$

$$M2 = F \times L2,$$

$$M3 = F \times L3.$$

Where, L1, L2, and L3 denote the lengths shown in FIG. 6.

The bending moment is analogous to a bending torque, and therefore bending torque=bending stiffness×bent angle is established. This means that the bending moment M can be calculated from the equation for the bending torque.

Figure 7:
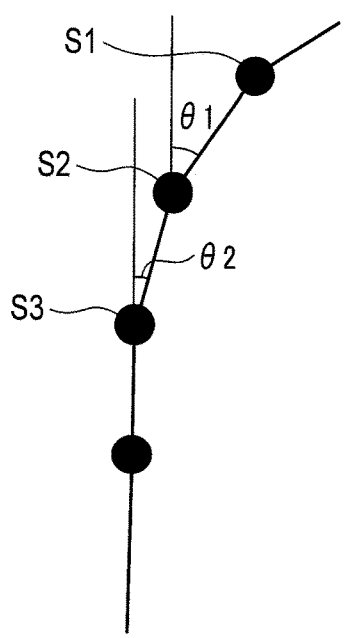
FIG. 7 is a diagram showing the bent angle of the flexible tube section, modeled with a link segment model.

FIG. 7 is a diagram of the flexible tube section 14 modeled with a link segment model. When the modeling points S1, S2, and S3 in the segments 14-1, 14-m, and 14-n shown in FIG. 6 are modeled as shown in FIG. 7, exemplary bent angles for the above bending torque equations are represented by θ1 and θ2. These bent angles can be obtained from the bent shape of the flexible tube section 14, in turn obtained from the state detection device 50. The base point determination section 116 can therefore calculate the bending moments of the flexible tube section 14, based on the shape information obtained from the state calculation section 115.

Figure 8:
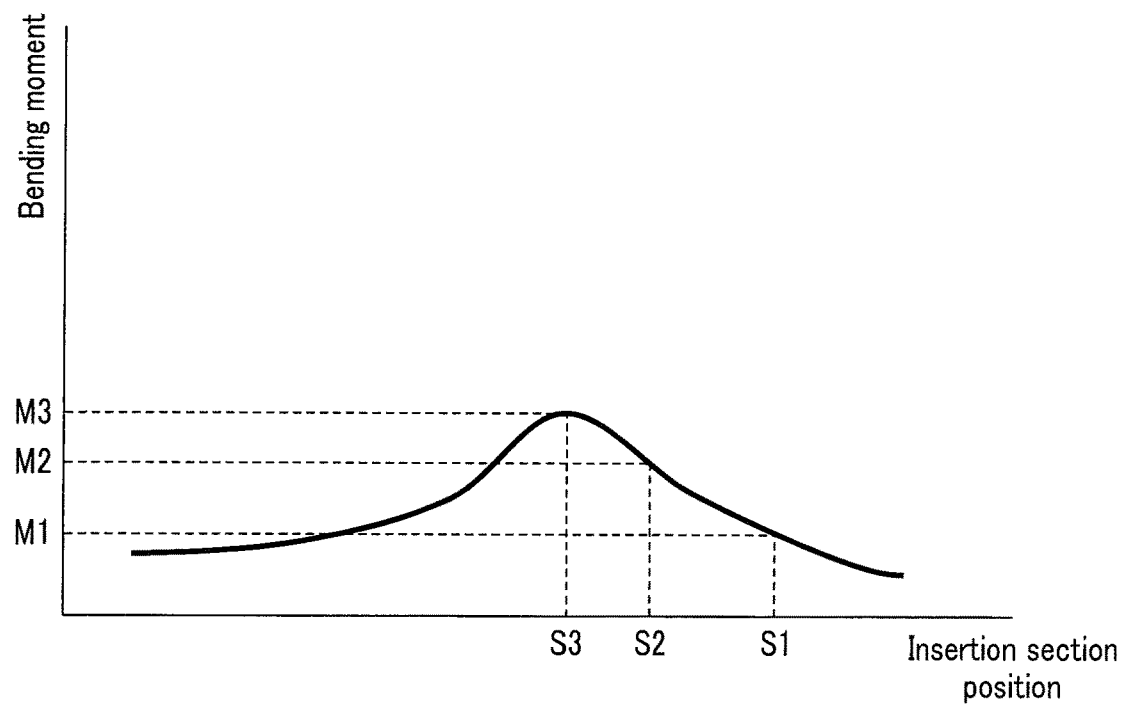
FIG. 8 is a diagram showing an exemplary relationship between the position of the insertion section and the bending moment.

FIG. 8 is a diagram showing an example of the relationship between the position of the insertion section when being inserted as shown in FIG. 6 and the bending moments. The horizontal axis of FIG. 8 represents the position of the insertion section, where the left side is the proximal end side (manipulating side) and the right side is the distal end side. The bending moments at points S1, S2, and S3 shown in FIG. 6 are indicated in FIG. 8 as M1, M2, and M3, respectively. The bending moment takes a local maximum value, here a maximum value M3, at point S3. Thus, under this situation, the flexible tube section 14 is most easy to bend at the point S3. Therefore, according to the present embodiment, the base point determination section 116 determines the point S3 where the bending moment is largest as the base point of the variation in bending stiffness. The stiffness controller 117 then applies a voltage from its variable stiffness output section to the corresponding variable stiffness unit 60 such that the bending stiffness of the portion the flexible tube section 14 that includes the base point S3 is reduced. In the present embodiment, the bending stiffness value is reduced at a place where the bending moment calculated using the state information and shape information of the flexible tube section 14 is large. That is, the bending stiffness value of the portion including the base point is reduced so that a place where the flexible tube section is easy to bend becomes yet easier to bend.

Figure 9:
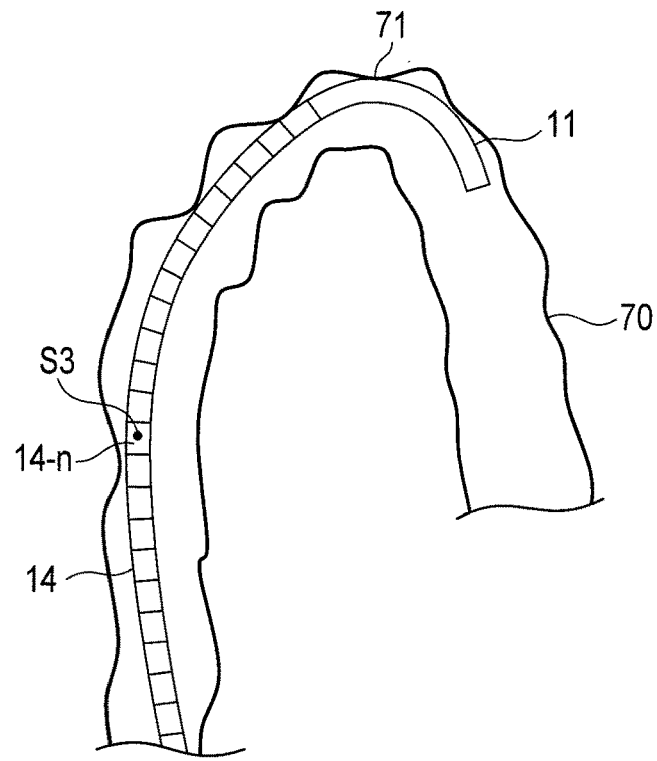
FIG. 9 is a diagram showing an example of the position of the base point of the variation in bending stiffness determined based on the degree of bending moment.
Figure 10:
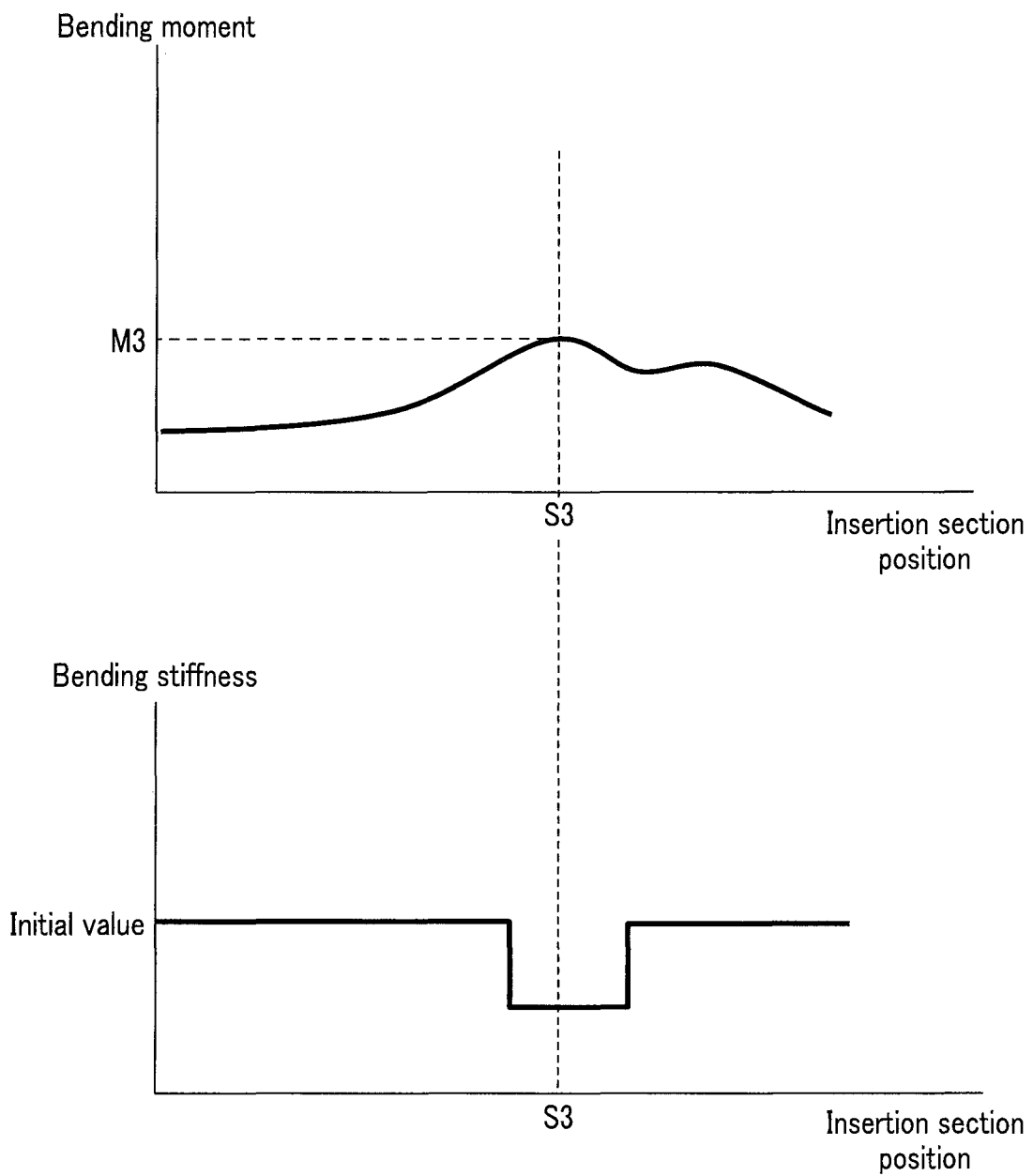
FIG. 10 is a diagram showing an exemplary relationship between the position of the insertion section, the bending moment, and the bending stiffness.

In the above example, the base point determination section 116 determines the point S3 of the flexible tube section 14 as the base point of the variation in bending stiffness, as shown in FIG. 9. Then, the stiffness controller 117 controls the voltage to be applied to the corresponding variable stiffness unit 60 from its variable stiffness output section so that the bending stiffness value of the variable stiffness unit 60 in the segment 14-n including the base point S3 is reduced. For example, as shown in FIG. 10, when the bending moment value is local maximal (largest) at the point S3, the stiffness controller 117 controls the voltage to be applied to the corresponding variable stiffness unit 60 so that the bending stiffness value in a periphery of the base point becomes lower than the initial value Ma. As a result, the periphery of the flexible tube section 14 including the base point P3 becomes to be easy to bend. The range of the periphery of the base point can be suitably determined by the surgeon. The range of the periphery of the base point may be only a segment including the base point, or the segment including the base point and its adjacent segment or segments.

Figure 11:
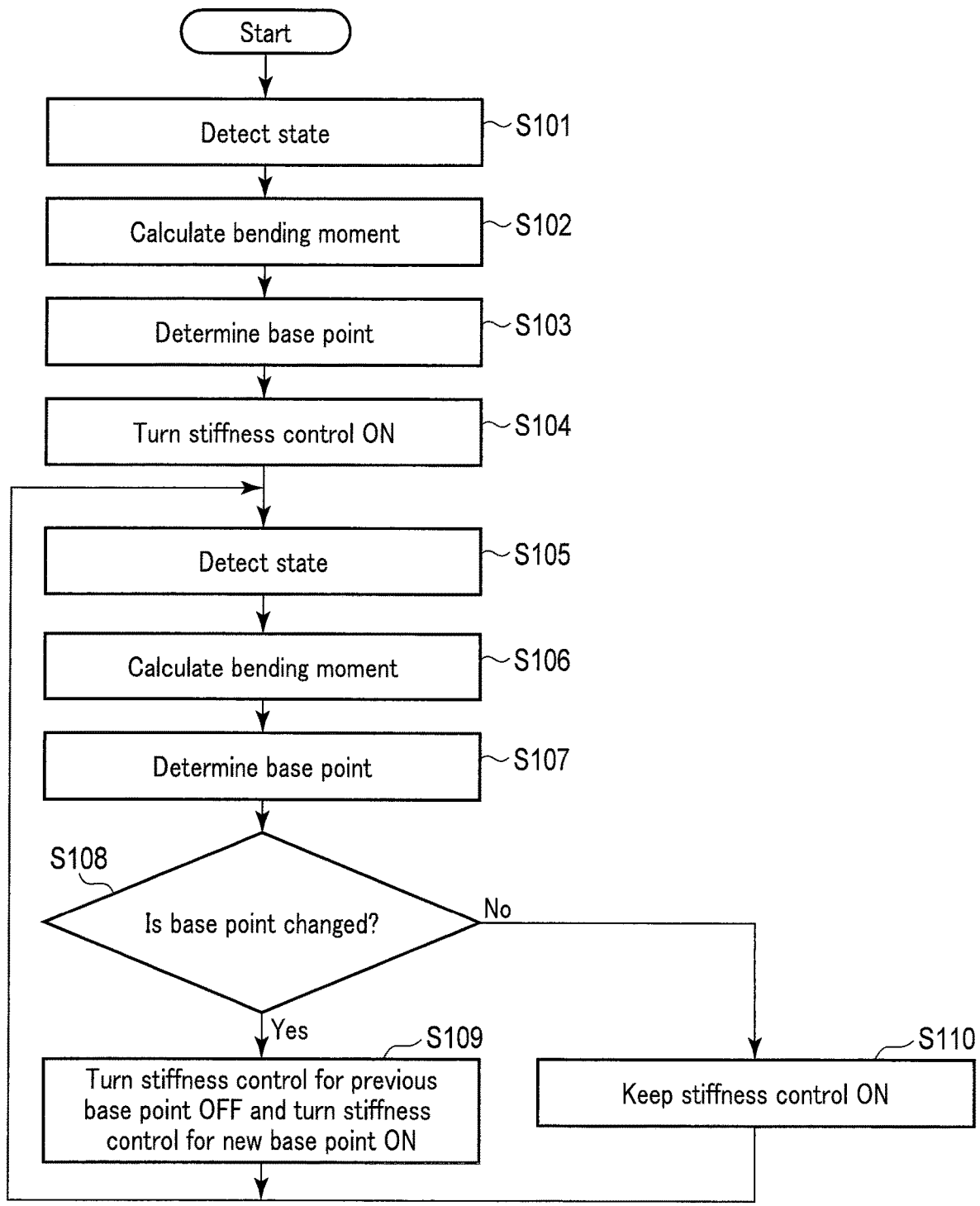
FIG. 11 is a diagram showing an exemplary flow of the bending stiffness control of the flexible tube section according to the first embodiment.

FIG. 11 shows an exemplary flow of the bending stiffness control of the flexible tube section 14 according to the present embodiment. At step S101, the state detection device 50 detects the state information of the flexible tube section 14, and then calculates the shape information based on the state information. At step S102, the base point determination section 116 calculates a bending moment based on the shape information. At step S103, the base point determination section 116 determines the base point of the variation in bending stiffness of the flexible tube section 14 based on the calculated bending moment. As described above, the determined base point of the variation in bending stiffness is a place where the flexible tube section is easy to bend, for example, the position of the flexible tube section 14 at which the value of the bending moment indicates the local maximum value or the maximum value. At step S104, the stiffness controller 117 reduces the bending stiffness of the variable stiffness units 60 in one or more segments including the base point of the flexible tube section 14 (the stiffness control is turned ON).

At step S105, the state detection device 50 detects the state information of the flexible tube section 14, and then calculates the shape information based on the state information. At step S106, the base point determination section 116 calculates the bending moment, based on the shape information. At step S107, the base point determination section 116 determines the base point of the variation in bending stiffness of the flexible tube section 14 based on the calculated bending moment. Then, at step S108, the base point determination section 116 compares the base point of the variation in bending stiffness for which the bending stiffness is currently varied with the base point newly determined at step S107, thereby determining whether or not the base point has been changed.

When the base point is changed at step S108 ("Yes"), the process proceeds to step S109. At step S109, the stiffness controller 117 sets the bending stiffness of the variable stiffness units 60 in the one or more segments including the base point for which the bending stiffness is currently varied back to the original value (the stiffness control is turned OFF), while the stiffness controller 117 reduces the bending stiffness of the variable stiffness units 60 in one or more segments including the base point that is newly determined at step S107 (the stiffness control is turned ON).

On the other hand, if the base point is not changed at step S108 ("No"), the process proceeds to step S110. At step S110, the stiffness controller 117 keeps the stiffness control ON. At step S110, the stiffness controller 117 may maintain the bending stiffness value of the variable stiffness units 60 in the one or more segments including the base point, or may reduce the bending stiffness value. After step S109 or S110, the process returns to step S105.

Figure 12:
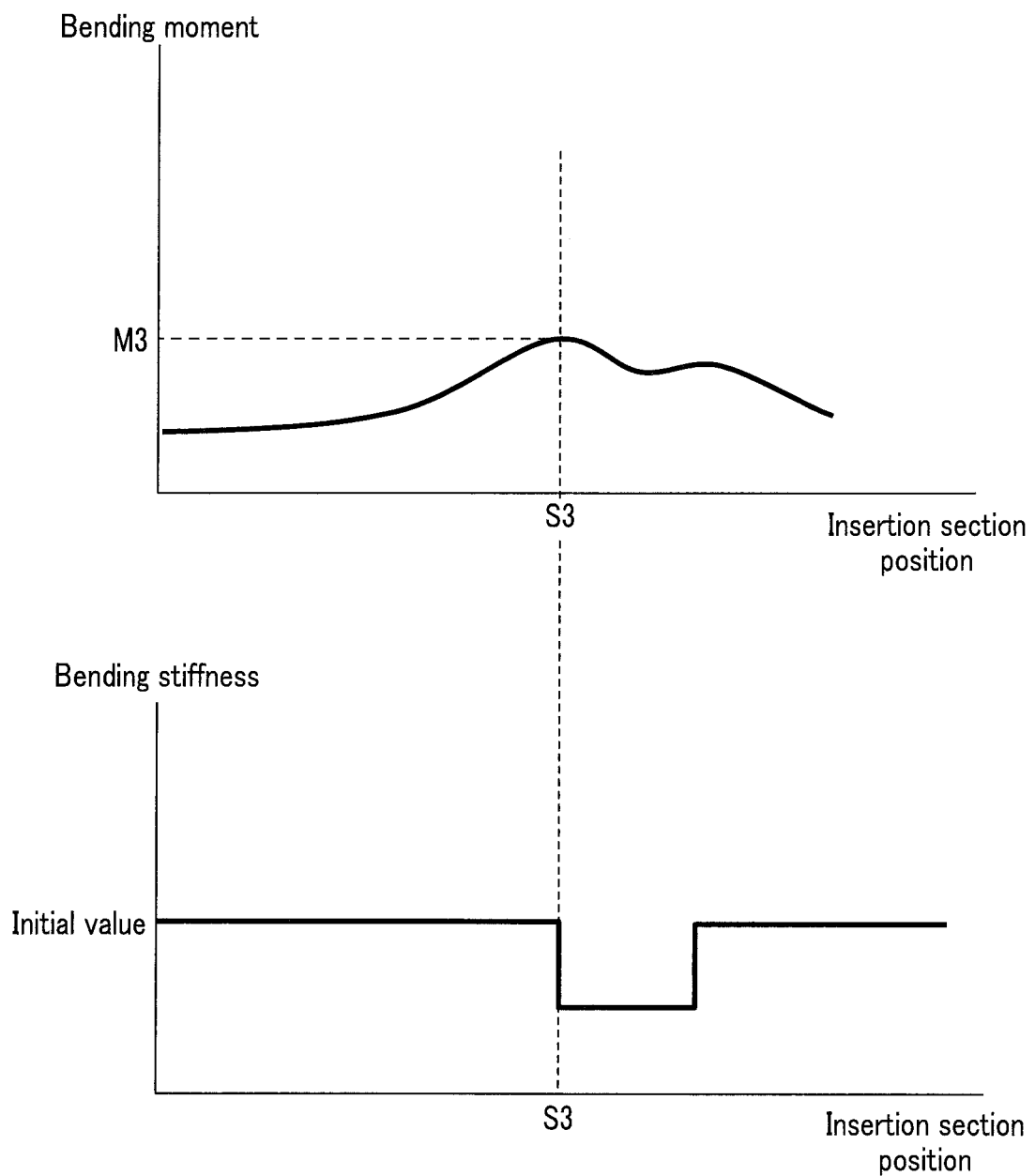
FIG. 12 is a diagram showing an exemplary relationship between the position of the insertion section, the bending moment, and the bending stiffness.

In the above description, the stiffness controller 117 reduces the bending stiffness of the variable stiffness units 60 in the segment including the base point of the variation in bending stiffness and its front and rear segments so as to render the flexible tube section 14 easy to bend (see FIG. 10). However, as shown in FIG. 12, the stiffness controller 117 may reduce the bending stiffness of the variable stiffness units 60 in the segments in a predetermined range on the distal end side with respect to the base point S3 serving as a starting point. That is, when the value of the bending moment is local maximal (the largest) at the point S3, the stiffness controller 117 controls the voltage to be applied to the corresponding variable stiffness units 60 so that the bending stiffness value at the distal end side including the base point becomes lower than the initial value Ma. With such control, a place where the flexible tube section is easy to bend including the base point becomes more flexible.

The endoscope apparatus 1 according to the present embodiment reduces the bending stiffness of a place where the flexible tube section 14 is easy to bend, i.e., a place where the bending moment is large, when the insertion section 11 passes through the flexure 71. The insertion section 11 bends under the external force received from the intestine tract at the flexure 71. By reducing the bending stiffness value of a place where the flexible tube section is easy to bend, the insertion section 11 bends in a direction not to push of the flexure 71, so that the force applied to the intestine tract is reduced. This also leads the distal end of the insertion section 11 forward, and the insertability of the insertion section 11 is thereby improved. That is, the present embodiment can provide a flexible tube insertion device or an insertion control device with improved insertability by appropriately varying the bending stiffness of the flexible tube section 14.

When the insertion target is the large intestine, the sigmoid colon and transverse colon are securely held, so as to easily move. When the flexible tube section 14 of the endoscope apparatus 1 is inserted into such an intestine tract, the flexible tube section 14 is bent along the intestine wall when passing through the flexure 71. At this time, if the surgeon exerts a force from the manipulating side and pushes the flexible tube section 14 further, the flexible tube section 14 may bend in the intestine tract in a direction different from the direction of force transmission. In this case, a propulsive force is not sufficiently given to the distal end of the flexible tube section, so that the degree of insertability is reduced. In contrast, according to the present embodiment, partial bending stiffness control is performed by appropriately varying the bending stiffness of the flexible tube section 14 based on the bending moment, so that the insertion can be proceeded without decrease in the propulsive force of the insertion section 11.

In addition, according to the present embodiment, since the force applied to the intestine tract is reduced, the strain on a patient is mitigated. For example, when the insertion section passes through the S-top, where the patient is most susceptible to pain among the intestine tract flexures of the large intestine, extension of the intestine tract is suppressed. Thus, a flexible tube insertion device or an insertion control device that can alleviate the patient's pain can be provided.

Second Embodiment

A second embodiment of the present invention will be described with reference to FIGS. 13 to 19. In the following explanation, portions different from the first embodiment will be mainly described. The same components as those of the first embodiment will be denoted by the same reference numerals as those of the first embodiment, and the description thereof will be omitted.

FIG. 13 is a block diagram showing an example of an endoscope apparatus 1a according to the second embodiment. The endoscope apparatus 1a includes an endoscope 10, a light source apparatus 20, an input device 30, a display device 40, and a control device 100a. In the present embodiment, the control device 100a includes a timing determination section 118 in addition to the components of the control device 100 according to the first embodiment. Similarly to the components of the control device 100a, the timing determination section 118 may also be composed by a processor such as a CPU, or ASIC, FPGA, or the like. The timing determination section 118 determines the timing for varying the bending stiffness of the variable stiffness units 60 that are to be controlled by the stiffness controller 117. As long as this function can be performed, the timing determination section 118 may be included in a control device that is different from the control device 100.

According to the present embodiment, the base point determination section 116 acquires the shape information calculated by the state calculation section 115, calculates the bending moment based on the acquired shape information, and determines the base point of the variation in bending stiffness. Furthermore, the timing determination section 118 determines the timing for varying the bending stiffness of the variable stiffness units 60 to be controlled by the stiffness controller 117, based on the shape information calculated by the state calculation section 115, the bending moment calculated by the base point determination section 116, and the base point of the variation in bending stiffness determined by the base point determination section 116. Based on the determined base point and determined timing, the stiffness controller 117 varies the bending stiffness of the control-target variable stiffness units 60. In particular, the timing determination section 118 determines that it is time for the stiffness controller 117 to start the bending stiffness control when the bending moment of the base point determined by the base point determination section 116 is greater than or equal to a predetermined threshold value. Moreover, the timing determination section 118 determines that it is time for the stiffness controller 117 to stop the bending stiffness control when the bending moment is less than the predetermined threshold value. The threshold value can be freely set by the surgeon. The threshold value may be set based on experience, for example, sense of the hands of a surgeon having experiences in endoscopic examination, to a degree that the patient would not feel pain.

Figure 14:
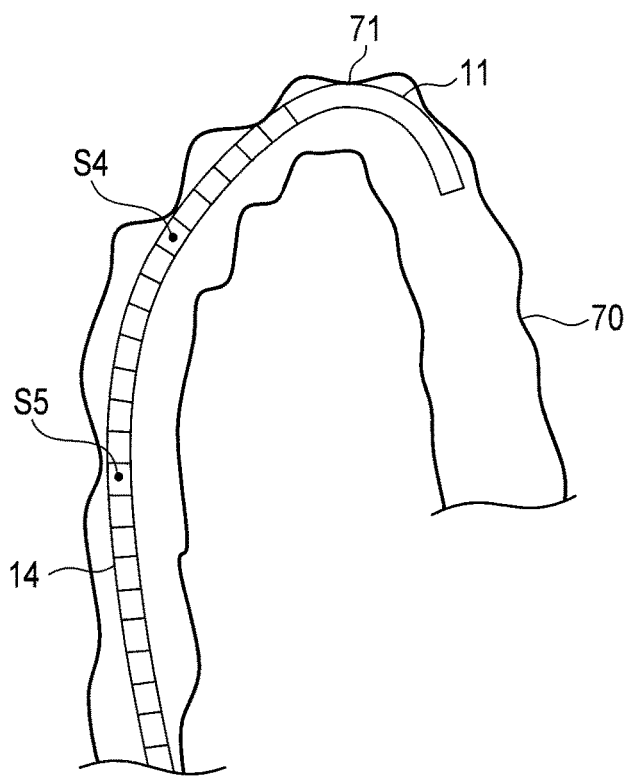
FIG. 14 is a diagram showing an example of the position of the base point of the variation in bending stiffness determined based on the degree of bending moment.
Figure 15:
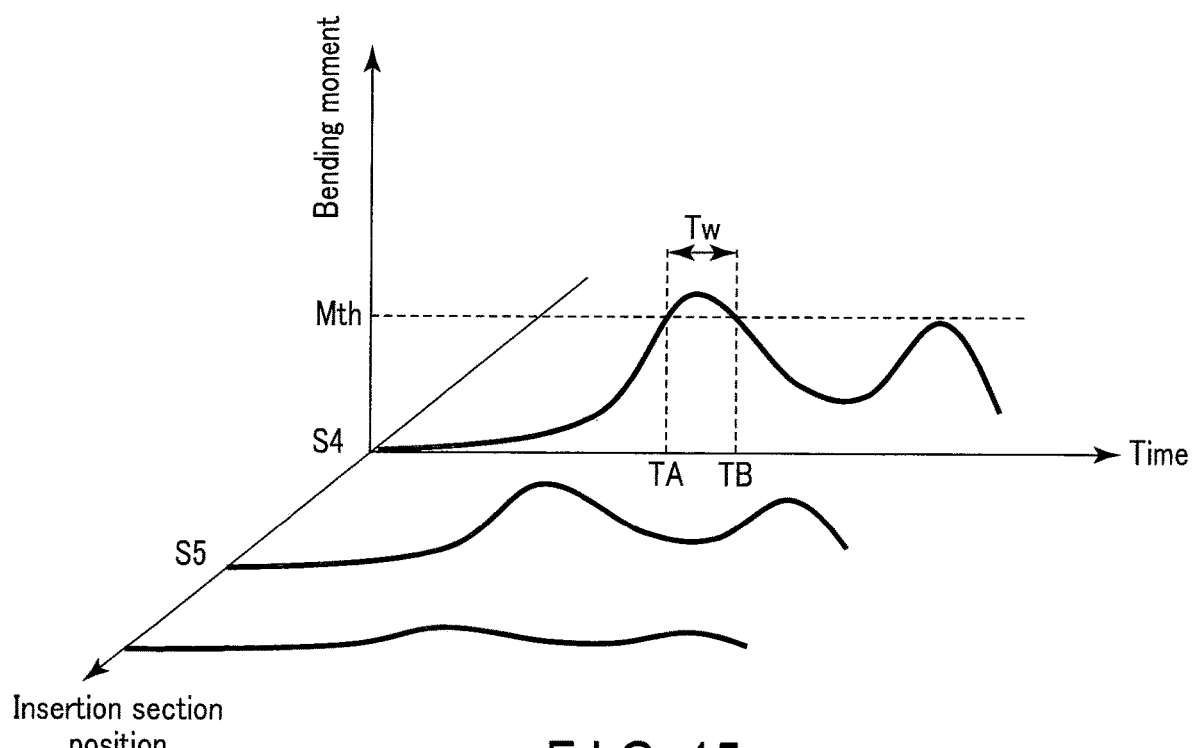
FIG. 15 is a diagram showing exemplary relationships among the position of the insertion section, time, and bending moment.

FIG. 15 shows an example of relationships among the positions of the insertion section, time, and bending moment, where the positions include points S4 and S5 in different segments of the flexible tube section 14 as shown in FIG. 14. For example, at time TA shown in FIG. 15, the base point determination section 116 determines the point S4 as the base point of the variation in bending stiffness based on the calculated bending moment. If the value of the bending moment M at the base point S4 is greater than or equal to the threshold value Mth, the timing determination section 118 determines this time TA as the timing for varying the bending stiffness. The stiffness controller 117 then starts the bending stiffness control (the stiffness control is turned ON). Alternatively, if the value of the bending moment M at the base point S4 is less than the threshold value Mth at time TB, which is later than the time TA when the stiffness control is turned on, the timing determination section 118 determines the time TB as the timing for varying the bending stiffness. The stiffness controller 117 then stops the bending stiffness control (the stiffness control is turned OFF). That is, the time period Tw from the time TA to the time TB is the time period during which the bending stiffness control is performed by the stiffness controller 117. During this time period Tw, the bending stiffness of the variable stiffness units 60 in one or more segments including the base point S4 of the flexible tube section 14 is reduced.

Figure 16:
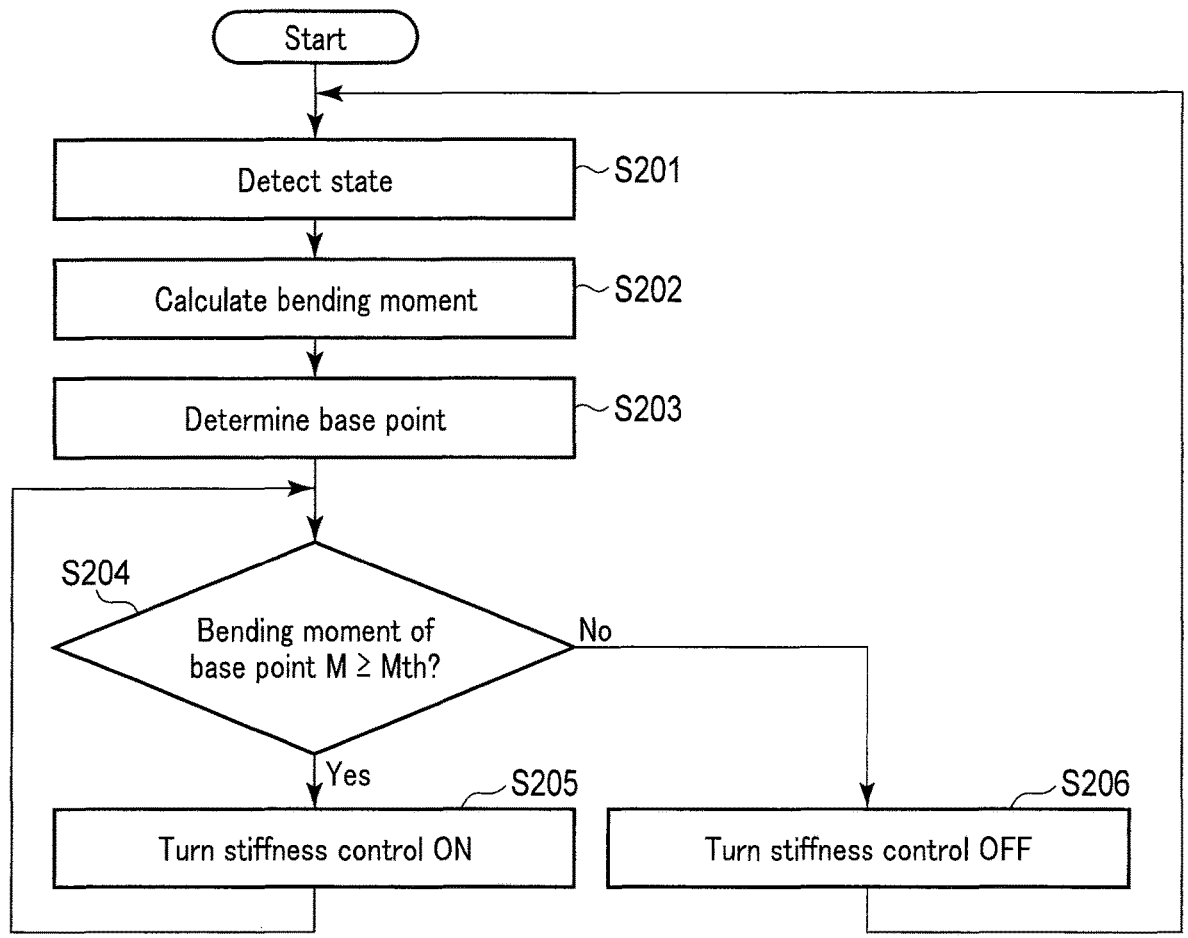
FIG. 16 is a diagram showing an exemplary flow of the bending stiffness control of the flexible tube section according to the second embodiment.

FIG. 16 is a diagram showing an exemplary flow of the bending stiffness control of the flexible tube section 14 according to the present embodiment. At step S201, the state detection device 50 detects the state information of the flexible tube section 14, and then calculates the shape information based on the state information. At step S202, the base point determination section 116 calculates a bending moment based on the shape information. At step S203, the base point determination section 116 determines the base point of the variation in bending stiffness of the flexible tube section 14 based on the calculated bending moment. Similar to the first embodiment, the base point may be a place where the flexible tube section is easy to bend, for example, the portion of the flexible tube section 14 at which the value of the bending moment indicates the local maximum value or the maximum value.

At step S204, the timing determination section 118 determines whether or not the bending moment M of the base point determined at step S203 is greater than or equal to the threshold value Mth. If the bending moment M is greater than or equal to the threshold value Mth ("Yes"), the process proceeds to step S205. At step S205, the stiffness controller 117 reduces the bending stiffness of the variable stiffness units 60 in one or more segments including the base point (the stiffness control is turned ON). After step S205, the process returns to step S204. On the other hand, if the bending moment M is less than the threshold value Mth at step S204 ("No"), the process proceeds to step S206. At step S206, the stiffness controller 117 no longer varies the bending stiffness of the variable stiffness units 60 in the one or more segments including the base point, or sets the bending stiffness back to the original value (the stiffness control is turned OFF). After step S206, the process returns to step S201.

Figure 17:
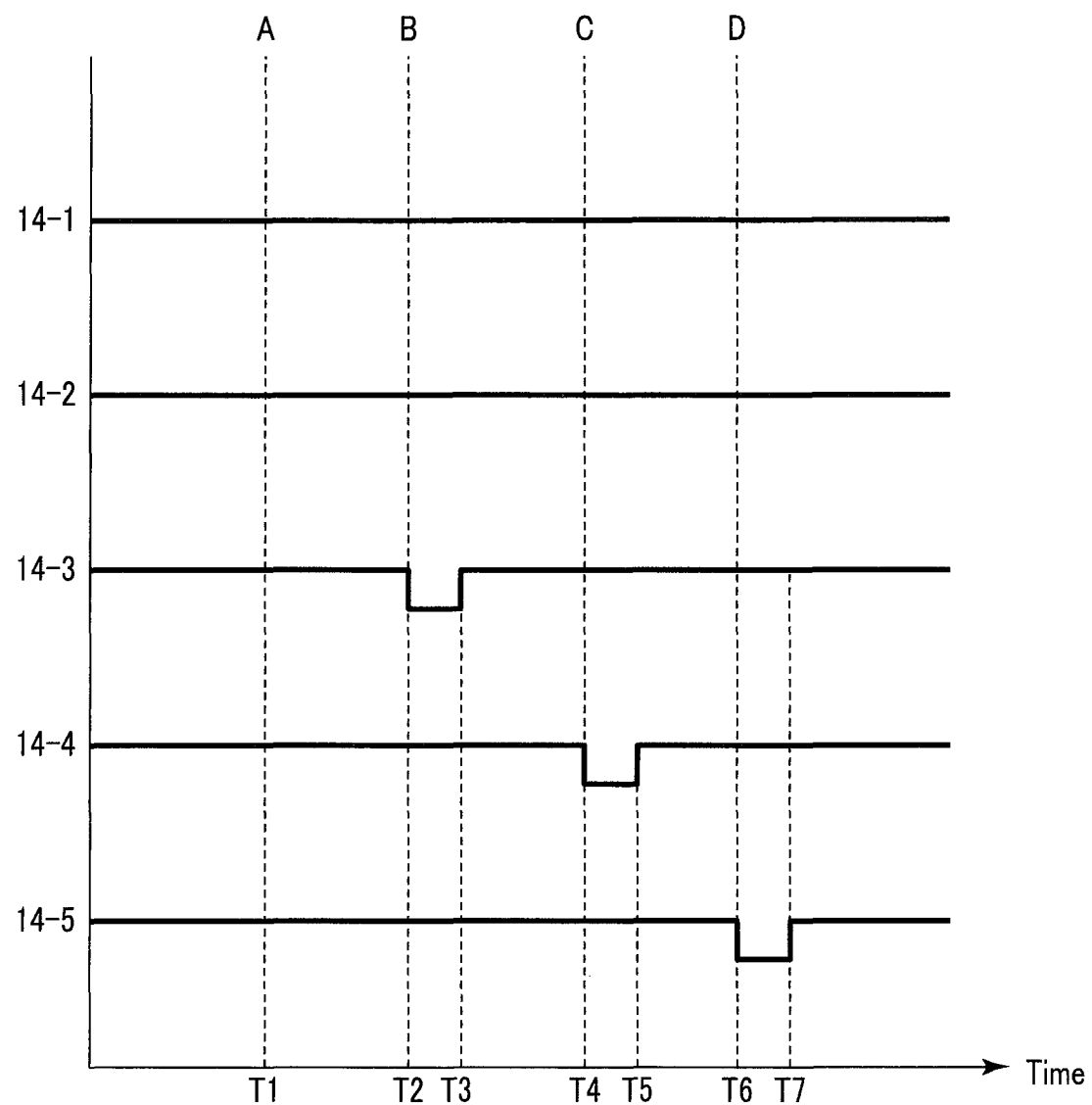
FIG. 17 is a diagram showing an exemplary timing chart of bending stiffness control.
Figure 18:
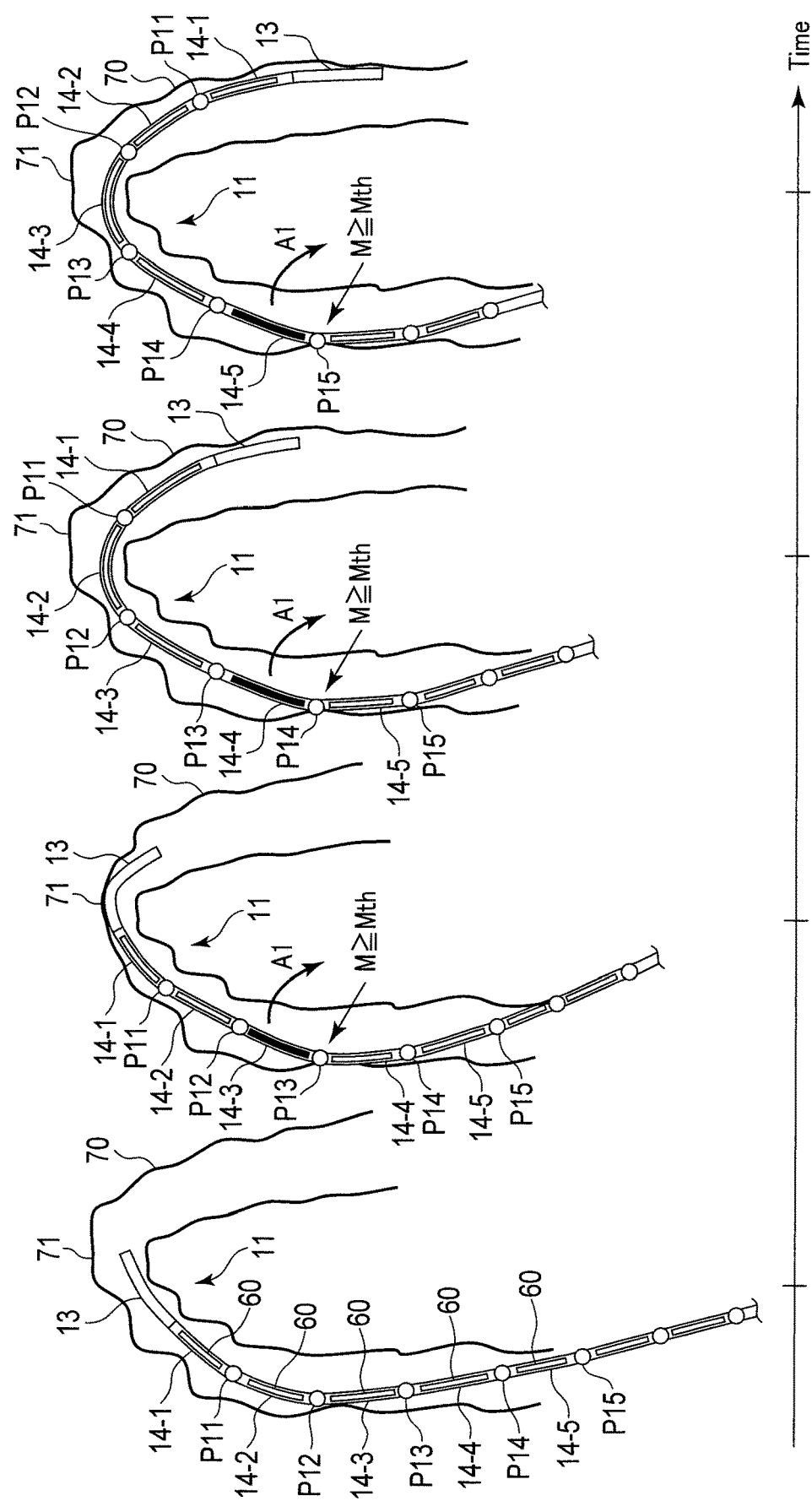
FIG. 18 shows an example of the bending stiffness control of the flexible tube section.

FIG. 17 is a timing chart showing an example of the bending stiffness control of the variable stiffness units 60 provided in the segments 14-1, 14-2, 14-3, 14-4, and 14-5 shown in FIG. 2, for example. FIG. 18 is a diagram that corresponds to time T1 (A in FIG. 18), time T2 (B in FIG. 18), time T3 (C in FIG. 18), and time T4 (D in FIG. 18) of FIG. 17, and shows the bending stiffness control of the insertion section 11 that is in the state of being inserted to the large intestine 70. With regard to A to D in the timeline of FIG. 18, among the variable stiffness units 60 provided for the segments 14-1 to 14-5, the segments having the variable stiffness units 60 whose bending stiffness has been varied by the stiffness controller 117 (the stiffness control is turned ON) are blackened, while the segments having the variable stiffness units 60 whose bending stiffness is unvaried are outlined (the stiffness control is turned OFF). It is assumed that, in A to D of FIG. 18, points P11, P12, P13, P14, and P15 on the posterior side of the segments 14-1, 14-2, 14-3, 14-4, and 14-5 are noted in relation to the variation in bending stiffness of the segments 14-1, 14-2, 14-3, 14-4, and 14-5, respectively.

At time T1, as shown as A in the timeline of FIG. 18, the flexible tube section 14 is moving in the intestine tract toward the flexure 71 of the large intestine 70. At this time, the bending stiffness control has not yet been started, so that the stiffness control remains OFF for any of the variable stiffness units 60 in the segments 14-1 to 14-5.

At time T2, the bendable section 13 at the distal end side of the insertion section 11 is approaching the flexure 71 as shown as B in the timeline of FIG. 18. At this time, the bending moment at the point P13 on the posterior side of the segment 14-3 in the flexible tube section 14 is greater than or equal to the threshold value. The stiffness controller 117 therefore varies the bending stiffness of the variable stiffness unit 60 provided in the segment 14-3 that includes at least the base point P13 (the stiffness control is turned ON). Thereby, for example, the bending stiffness value of the vicinity of the base point P13 is reduced to a level smaller than the initial value Ma. As a result, the segment 14-3 becomes more flexible and easier to bend in the direction indicated by arrow A1. Thereafter, at time T3, when the bending moment at the base point P13 on the posterior side of the segment 14-3 is less than the threshold value, the stiffness controller 117 sets the bending stiffness of the variable stiffness unit 60 provided in the segment 14-3 back to the original value (the stiffness control is turned OFF).

At time T4, as shown as C in the timeline of FIG. 18, the segment 14-1 of the flexible tube section 14 has passed through the flexure 71, and the following segment 14-2 is approaching the flexure 71. Here, in the flexible tube section 14, the bending moment at point P14 on the posterior side of the segment 14-4 is greater than or equal to the threshold value. Thus, the stiffness controller 117 varies the bending stiffness of the variable stiffness unit 60 provided in the segment 14-4 including the base point P14 (the stiffness control is turned ON). Thereby, for example, the bending stiffness value of the vicinity of the base point P14 is reduced to be smaller than the initial value Ma. The segment 14-4 becomes more flexible and easier to bend in the direction indicated by the arrow A1. Thereafter, at time T5, when the bending moment at the point P14 on the posterior side of the segment 14-4 is less than the threshold value, the stiffness controller 117 sets the bending stiffness of the variable stiffness unit 60 provided in the segment 14-4 back to the original value (the stiffness control is turned OFF).

At time T6, as shown as D in the timeline of FIG. 18, the segment 14-2 of flexible tube section 14 has passed through the flexure, and the following segment 14-3 is approaching the flexure 71. Here, in the flexible tube section 14, the bending moment at the point P15 on the posterior side of the segment 14-5 is greater than or equal to the threshold value. Thus, the stiffness controller 117 varies the bending stiffness of the variable stiffness unit 60 provided at least in the segment 14-5 including the base point P15 (the stiffness control is turned ON). Thereby, for example, the bending stiffness value of the vicinity of the base point P15 is reduced to be smaller than the initial value Ma. As a result, the segment 14-5 becomes more flexible and easier to bend in the direction indicated by arrow A1. Thereafter, at time T7, when the bending moment at the point P15 on the posterior side of the segment 14-5 is less than the threshold value, the stiffness controller 117 sets the bending stiffness of the variable stiffness unit 60 provided in the segment 14-5 back to the original value (the stiffness control is turned OFF).

By repeating the above cycle, the stiffness controller 117 sequentially reduces the bending stiffness of the variable stiffness unit 60 corresponding to the portion where the value of the bending moment of the base point is greater than or equal to the threshold value.

As described above, according to the present embodiment, the timing determination section 118 determines to start the bending stiffness control when the bending moment is greater than or equal to the predetermined threshold value, and to stop the bending stiffness control when the bending moment is less than the predetermined threshold value. By such a control, a flexible tube insertion device or an insertion control device that has an insertability improved by appropriately varying the bending stiffness of the flexible tube section 14 is provided.

Figure 19:
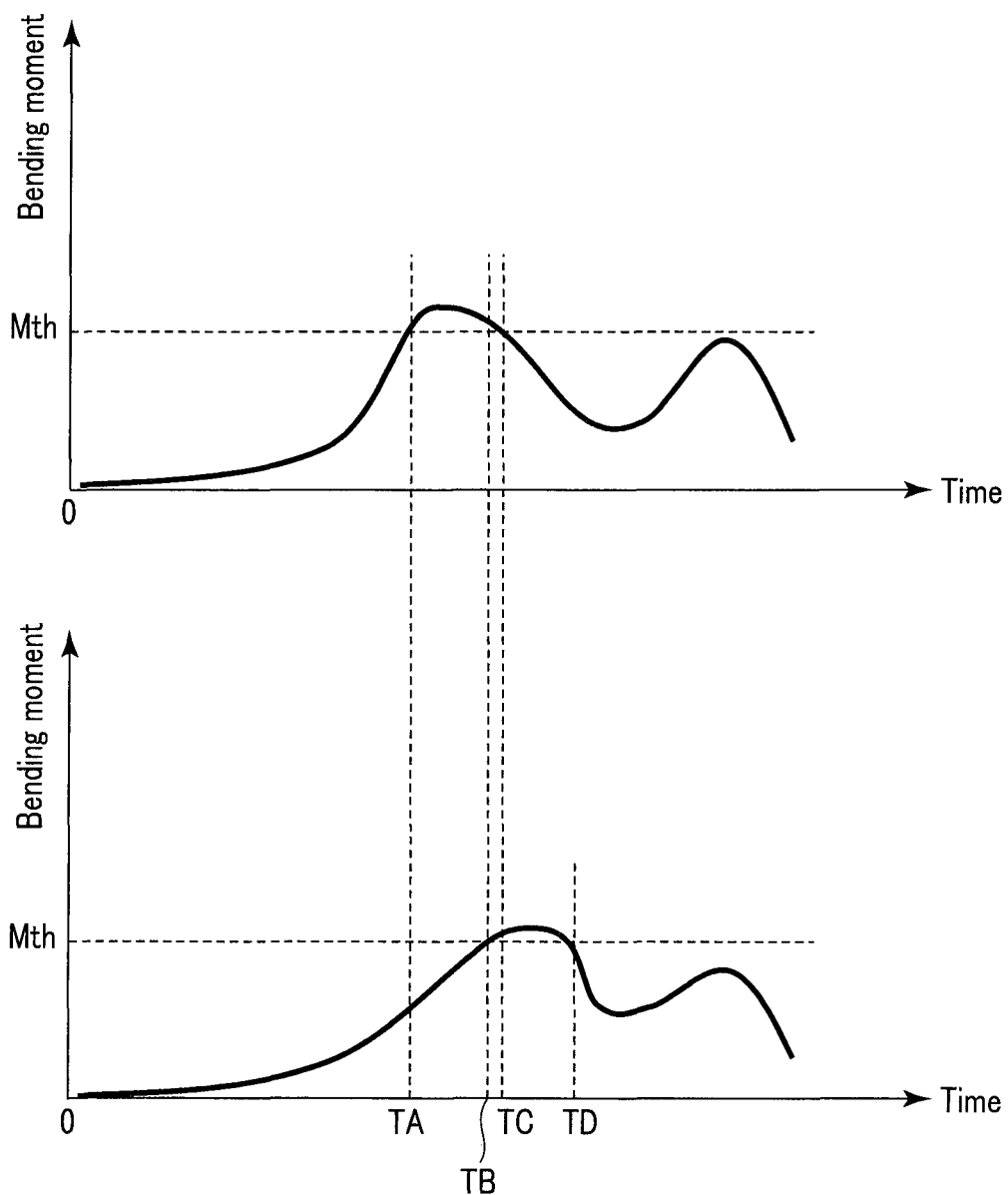
FIG. 19 is a diagram showing an exemplary relationship between the bending moment and time when the bending stiffness is varied at two positions.

In FIG. 15, the bending moment exceeds the threshold value Mth only at the point S4. However, if the bending moment value exceeds the threshold value at multiple positions of the flexible tube section 14, the bending stiffness may be varied at the multiple positions. In FIG. 19, the upper half shows an exemplary relationship between the time and bending moment at point S4 of FIG. 14, and the lower half shows an exemplary relationship between the time and bending moment at point S5 in FIG. 14.

For example, at the time TA, the base point determination section 116 determines the point S4 as the base point of the variation in bending stiffness based on the calculated bending moment. If the value of the bending moment M at the base point S4 is greater than or equal to the threshold value Mth, the timing determination section 118 determines this time TA as the timing for varying the bending stiffness. In response, the stiffness controller 117 starts the bending stiffness control (the stiffness control is turned ON).

Furthermore, at the time TB, which is later than the time TA, the base point determination section 116 determines the point S5 as the base point of the variation in bending stiffness based on the calculated bending moment. If the value of the bending moment M at the base point S5 is greater than or equal to the threshold value Mth, the timing determination section 118 determines this time TB as the timing for varying the bending stiffness. In response, the stiffness controller 117 starts the bending stiffness control (the stiffness control is turned ON).

If the value of the bending moment M at the base point S4 is less than the threshold value Mth at time TC, which is later than the time TB, the timing determination section 118 determines the time TC as the timing for varying the bending stiffness. In response, the stiffness controller 117 stops the bending stiffness control (the stiffness control is turned OFF).

Furthermore, if the value of the bending moment M at the base point S5 is less than the threshold value Mth at time TD that is later than the time TC, the timing determination section 118 determines the time TD as the timing for varying the bending stiffness. In response, the stiffness controller 117 stops the bending stiffness control (the stiffness control is turned OFF).

As discussed above, when the value of the bending moment exceeds the threshold value at multiple positions of the flexible tube section 14, the timing determination section 118 may determine the control timings so that the bending stiffness control is performed at the multiple positions of the variation in bending stiffness. The threshold value may be set to the same value or different values for multiple positions of the variation in bending stiffness.

Third Embodiment

A third embodiment of the present invention will be described with reference to FIGS. 20 to 28. In the following explanation, portions different from the second embodiment will be mainly described. The same components as those of the second embodiment will be denoted by the same reference numerals as those of the second embodiment, and the description thereof will be omitted.

FIG. 20 is a block diagram showing part of the configuration of the endoscope 210 and the control device 100a of an endoscope apparatus according to the third embodiment. The endoscope 210 has bent state detectors 55, external force detectors 56, and variable stiffness units 60. The bent state detector 55 is configured to detect the state information for calculating the bent shape (bent angle, bent amount, curvature or curvature radius, etc.) of the insertion section 11. The bent state detector 55 may be the source coil 52 of the first embodiment or the like. In this case, similar to the first embodiment, the source coils 52 of the source coil array 53, the antenna 54, the coil controller 114, and state calculation section 115 of the control device 100a may constitute the bent shape detection device 51.

According to the present embodiment, the endoscope 210 includes external force detectors 56. Exemplary external force detectors 56 are illustrated in FIG. 21. The external force detector 56 may be a sensor 57 arranged on the outer peripheral surface of the insertion section 11. The sensor 57 may be of any type that can detect an external force applied to the outer peripheral surface of the insertion section 11, such as a pressure sensor. In FIG. 21, the sensors 57 are arranged at intervals in the axial direction of the flexible tube section 14. The sensors 57 are arranged also in the bendable section 13 as well as in the flexible tube section 14. That is, the sensors 57 can detect an external force applied to the bendable section 13 and the flexible tube section 14. The sensors 57 are connected to the state calculation section 115. The external force detector 56 detects the external force applied to the bendable section 13 and the flexible tube section 14, and then transmits the detected amounts of external force to the state calculation section 115. The external force applied to the bendable section 13 and the flexible tube section 14 may be a contact pressure received from the flexure of the intestine tract when the bendable section 13 and the flexible tube section 14 is in contact with the flexure of the intestine tract.

According to the third embodiment, the endoscope apparatus has state detectors 58 that include the bent state detectors 55 and the external force detectors 56 and are configured to detect information on the state of the bendable section 13 and the flexible tube section 14 of the insertion section 11.

Similar to the second embodiment, the control device 100a includes a state calculation section 115, a base point determination section 116, a stiffness controller 117, and a timing determination section 118. The control device 100a also includes the light source controller 111, the image processor 112, the display controller 113, and the coil controller 114, although these components are not shown for simplification of the drawing. According to the present embodiment, the timing determination section 118 determines the timing for starting the bending stiffness control when the contact pressure on the flexible tube section 14 at the contact point is greater than or equal to a predetermined threshold value, based on the contact pressure information calculated by the state calculation section 115, in turn based on the information obtained from the external force detectors 56 that serve as the state detectors 58. Alternatively, the timing determination section 118 determines the timing for stopping the bending stiffness control when the contact pressure on the flexible tube section 14 at the contact point is less than the predetermined threshold value, based on the contact pressure information calculated from the information obtained from the external force detectors 56 that serve as the state detector. The threshold value can be freely set by the surgeon. The threshold value may be set based on experience, for example, sense of the hands of a surgeon having experiences in endoscopic examination, to a degree that the patient would not feel pain. As described above, according to the present embodiment, the bending moment information is used for the determination of the base point of the bending stiffness control, and the contact pressure information is used for the determination of the timing for the bending stiffness control.

Figure 23:
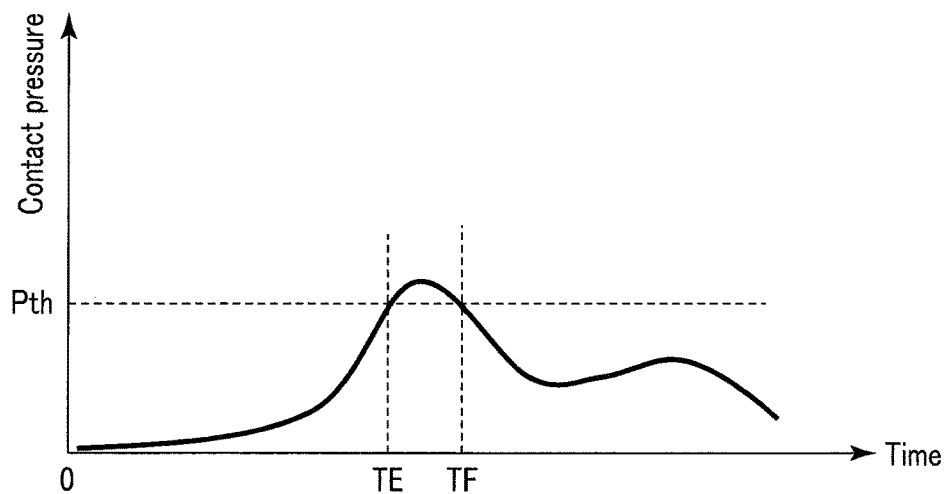
FIG. 23 shows an exemplary relationship between time and contact pressure.

FIG. 22 is a diagram illustrating an exemplary contact state between the insertion section 11 and the flexure 71. FIG. 23 is a diagram showing an exemplary relationship between time and contact pressure. As shown in FIG. 22, it is assumed that the insertion section 11 in contact with the flexure is under a contact pressure P. For example, if the contact pressure P is greater than or equal to a threshold value Pth at time TE, the timing determination section 118 determines this time TE as a timing for varying the bending stiffness. In response, the stiffness controller 117 starts the bending stiffness control (the stiffness control is turned ON). Alternatively, for example, if the contact pressure P is less than the threshold value Pth at time TF, which is later than the time TE, the timing determination section 118 determines time TF as a timing for varying the bending stiffness. In response, the stiffness controller 117 stops the bending stiffness control (the stiffness control is turned OFF).

Figure 24:
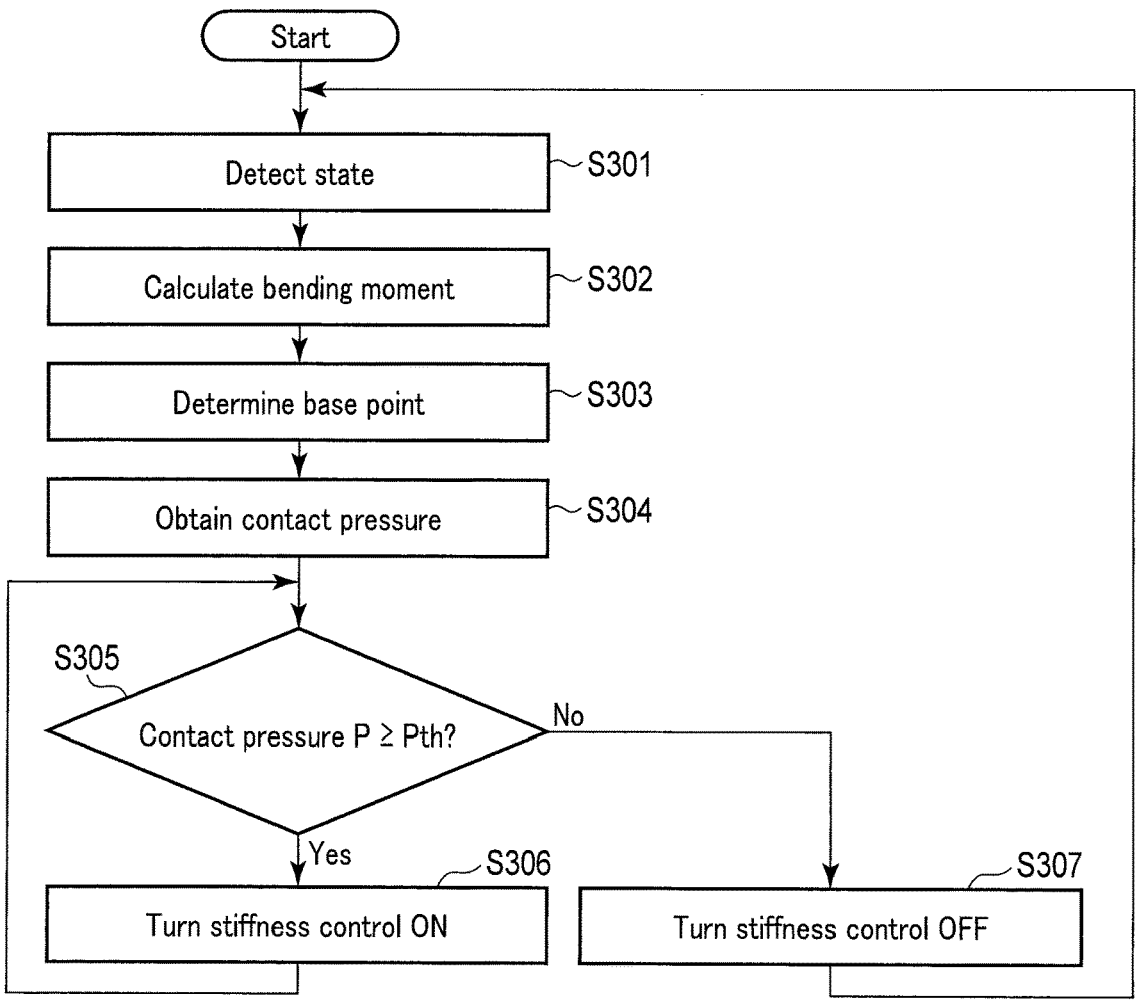
FIG. 24 is a diagram showing an exemplary flow of bending stiffness control of the flexible tube section according to the third embodiment.

FIG. 24 is a diagram showing the flow of the bending stiffness control of the flexible tube section 14 according to the present embodiment. At step S301, the state detector 58 detects the state information of the bendable section 13 and the flexible tube section 14, and the state calculation section 115 calculates the shape information and contact pressure information based on the state information. At step S302, the base point determination section 116 calculates a bending moment based on the state information. At step S303, the base point determination section 116 determines the base point of the variation in bending stiffness of the flexible tube section 14 based on the calculated bending moment. Similar to the first embodiment, the base point may be a place where the flexible tube section 14 is easy to bend, for example, the position of the flexible tube section 14 at which the value of the bending moment indicates the local maximum value or the maximum value.

At step S304, the timing determination section 118 acquires the contact pressure information calculated by the state calculation section 115. At step S305, the timing determination section 118 determines whether or not the contact pressure P is greater than or equal to the threshold value Pth. If the contact pressure is greater than or equal to the threshold value Pth ("Yes"), the process proceeds to step S306. At step S306, the stiffness controller 117 varies the bending stiffness of the variable stiffness units 60 in one or more segments including the base point (stiffness control is turned ON). After step S306, the process returns to step S305. On the other hand, if the contact pressure P is less than the threshold value Pth ("No"), the process proceeds to step S307. At step S307, the stiffness controller 117 no longer varies the bending stiffness of the variable stiffness units 60 of the one or more segments including the base point, or sets the bending stiffness back to the original value (the stiffness control is turned OFF). After step S307, the process returns to step S301.

FIG. 25 is a diagram showing an example of the bending stiffness control of the variable stiffness units 60 provided in the segments 14-1 and 14-2 shown in FIG. 2. In a similar manner to FIG. 18, among the variable stiffness units 60 provided in the segments 14-1 and 14-2 in FIG. 25, the segments having the variable stiffness units 60 whose bending stiffness has been varied by the stiffness controller 117 (the stiffness control is turned ON) are blackened, while the segments having the variable stiffness units 60 whose bending stiffness is unvaried (the stiffness control is turned OFF) are outlined. Furthermore, it is assumed that points P21 and P22 on the posterior side of the segments 14-1 and 14-2, respectively, are noted in relation to the variation in bending stiffness in the segments.

In the state illustrated on the left side of FIG. 25, the flexible tube section 14 is moving inside the intestine tract towards the flexure 71 of the large intestine 70. At this time, the bending stiffness control has not yet been started, so that the stiffness control remains OFF for the variable stiffness units 60 provided in the segments 14-1 and 14-2.

In the state illustrated in the middle of FIG. 25, the bendable section 13 at the distal end side of the insertion section 11 is contact with the flexure 71, so as to receive an external force, i.e., contact pressure P, from the flexure 71. The contact pressure P is detected by the external force detector 56 (not shown). When this contact pressure P exceeds the threshold value Pth, the bending stiffness of the variable stiffness unit 60 in the segment 14-2 that includes the base point P2 on the posterior side of the segment 14-2 is reduced by the stiffness controller 117 (the stiffness control is turned ON).

In the state illustrated on the right side of FIG. 25, the segment 14-1 of the flexible tube section 14 has passed through the flexure 71, so that the bendable section 13 or flexible tube section 14 is not in contact with the flexure 71. The segment 14-2 is in contact with the intestine wall but not with the flexure 71, so that the contact pressure P is small. Thus, the contact pressure P detected by any of the external force detectors 56 does not exceed the threshold value Pth. For this reason, the bending stiffness of the variable stiffness unit 60 in the segment 14-2 including the base point P2 on the posterior side of the segment 14-2 is set back to the original value (the stiffness control is turned OFF). Here, since the bendable section 13 and the flexible tube section 14 are not under the contact pressure that exceeds the threshold value Pth, the bending stiffness of the variable stiffness units 60 is not varied.

Also in the present embodiment, a flexible tube insertion device or an insertion control device with improved insertability by suitably varying the bending stiffness of the flexible tube section 14 can be provided.

In the above description, the large intestine endoscope is adopted as an example of a transanal endoscope, which is not a limitation of the endoscope. The concept of the present invention can be applied not only to a lower gastrointestinal endoscope, which is transanally inserted, but also to an upper gastrointestinal endoscope, which is orally or nasally inserted. In particular, the application of the third embodiment is effective in a nasal endoscope. FIG. 26 is a diagram showing an example of bending stiffness control of a nasal endoscope having a variable stiffness unit 60.

The insertion section 11 of the nasal endoscope is inserted through the nostril 80 as shown on the left side of FIG. 26. For example, the insertion section 11 is inserted between the middle turbinate 81 and the lower turbinate 82 into the pharynx and esophagus. At the beginning of the insertion, the stiffness control is OFF for the variable stiffness unit 60 in the segment 14-1.

As shown in the middle of FIG. 26, the bendable section 13 is in contact with the middle turbinate 81, so as to receive a contact pressure P. When this contact pressure P exceeds the threshold value Pth, the stiffness controller 117 reduces the bending stiffness value of the variable stiffness unit 60 provided in the segment 14-1 in the vicinity of the point where the bending moment is largest (the stiffness control is turned ON).

In the state illustrated on the right side of FIG. 26, the bendable section 13 has passed between the middle turbinate 81 and the lower turbinate 82, so that a portion of the flexible tube section 14 at the proximal end side of the bendable section 13 is not contact with the middle turbinate. Here, the contact pressure P does not exceed the threshold value Pth. The bending stiffness of the variable stiffness unit 60 in the segment 14-1 is therefore set back to the original value (the stiffness control is turned OFF). Furthermore, with neither the bendable section 13 nor the flexible tube section 14 receiving a contact pressure P that exceeds the threshold value Pth, the variable stiffness units 60 are not subjected to the variation in bending stiffness.

The embodiments of the present invention have been described above. The bending stiffness control may also be performed based on the determination of the base point as described below.

Figure 27:
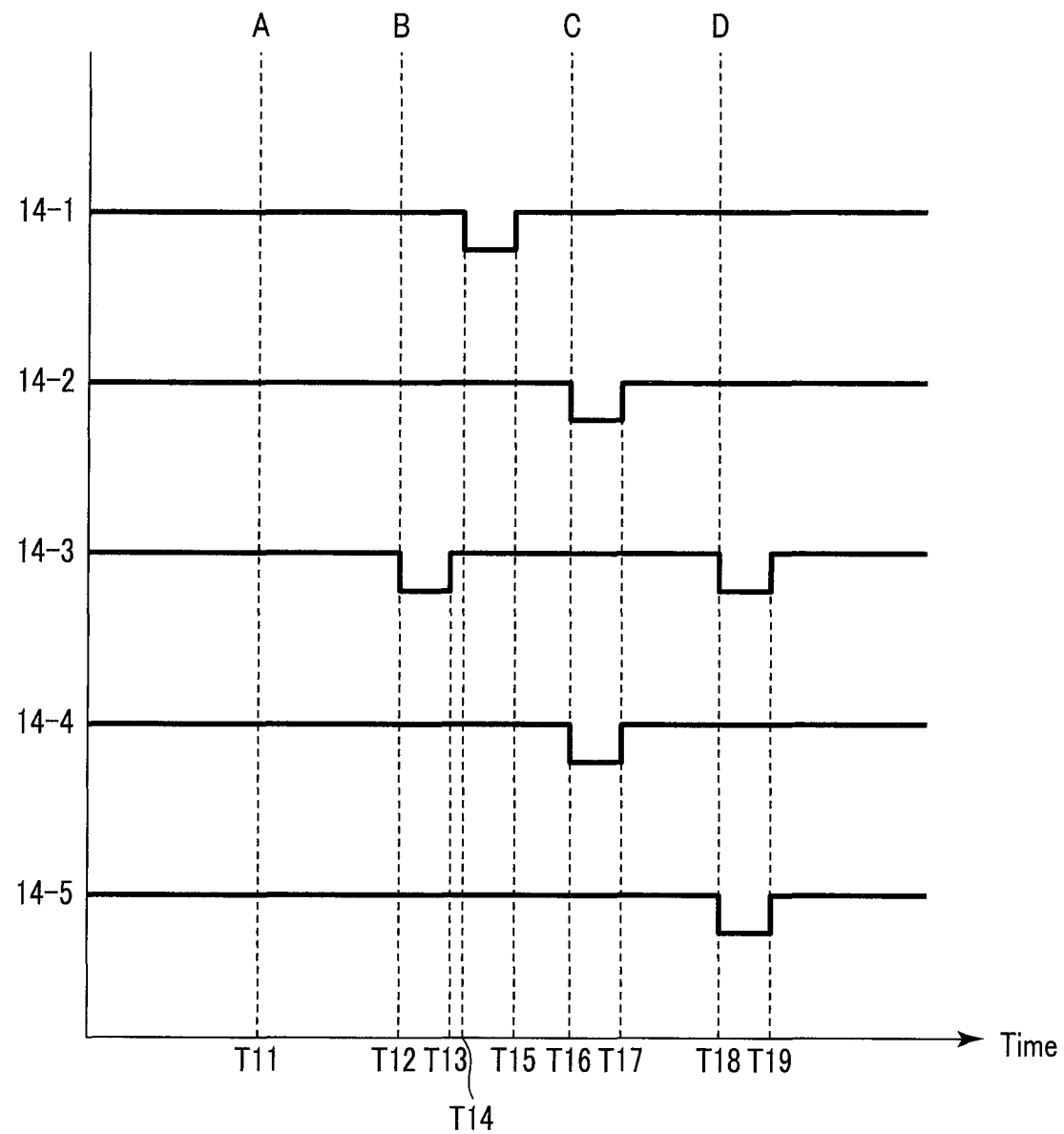
FIG. 27 is a diagram showing an exemplary timing chart of bending stiffness control.

FIG. 27 is a timing chart showing an example of the bending stiffness control of the variable stiffness units 60 provided in the segments 14-1, 14-2, 14-3, 14-4, and 14-5 of FIG. 2. FIG. 28 is a diagram that shows the bending stiffness control of the insertion section 11 that is in the inserted states corresponding to time T11 (A in FIG. 28), time T12 (B in FIG. 28), time T16 (C in FIG. 28), and time T18 (D in FIG. 28) of FIG. 27. In a similar manner to FIG. 18, in A to D in the timeline of FIG. 28, among the variable stiffness units 60 provided in the segments 14-1 to 14-5, the segments having the variable stiffness units 60 whose bending stiffness has been varied (the stiffness control is turned ON) are blackened, while the segments having the variable stiffness units 60 whose bending stiffness is unvaried (the stiffness control is turned OFF) are outlined. Similar to FIG. 18, it is assumed that, in A to D of FIG. 28, points P11, P12, P13, P14, and P15 on the posterior side of respective segments are noted in relation to the variation in bending stiffness in the segments 14-1, 14-2, 14-3, 14-4 and 14-5, respectively.

At time T11, as shown as A in the timeline of FIG. 28, the flexible tube section 14 is moving in the intestine tract toward the flexure 71 of the large intestine 70. At this time, the bending stiffness control has not yet been started, so that the stiffness control remains OFF for any of the variable stiffness units 60 in the segments 14-1 to 14-5.

At time T12, the bendable section 13 at the distal end side of the insertion section 11 is approaching the flexure 71 as shown as B in the timeline of FIG. 28. At this time, the bending moment at the point P13 on the posterior side of the segment 14-3 in the flexible tube section 14 is greater than or equal to the threshold value. The stiffness controller 117 therefore reduces the bending stiffness of the variable stiffness unit 60 provided in the segment 14-3 that includes at least the base point P13 (the stiffness control is turned ON). As a result, the segment 14-3 becomes more flexible and easier to bend in the direction indicated by arrow A1. Thereafter, at time T13, when the bending moment at the base point P13 on the posterior side of the segment 14-3 is less than the threshold value, the stiffness controller 117 sets the bending stiffness of the variable stiffness unit 60 provided in the segment 14-3 back to the original value (the stiffness control is turned OFF).

At time T14, the bendable section 13 at the distal end side of the insertion section 11 has passed through the flexure 71, and the segment 14-1 of the flexible tube section 14 is approaching the flexure 71. At this time, the segment 14-1 of the flexible tube section 14 is in contact with the flexure 71, so that the contact pressure P at the point P11 on the posterior side of the segment 14-1 is greater than or equal to the threshold value. In this case, the stiffness controller 117 varies the bending stiffness of the variable stiffness unit 60 in the segment 14-1 (the stiffness control is turned ON). Thereafter, at time T15, when the contact pressure P at the point P11 on the posterior side of the segment 14-1 is less than the threshold value, the stiffness controller 117 sets the bending stiffness of the variable stiffness unit 60 in the segment 14-1 back to the original value (the stiffness control is turned OFF).

At time T16, as shown as C in the timeline of FIG. 28, the segment 14-1 of the flexible tube section 14 has passed through the flexure 71, and the following segment 14-2 on the posterior side is approaching the flexure 71. At this time, the segment 14-2 of the flexible tube section 14 is in contact with the flexure 71, so that the contact pressure at the point P12 on the posterior side of the segment 14-2 is greater than or equal to the threshold value. In addition, the bending moment at the point P14 on the posterior side of the segment 14-4 is greater than or equal to the threshold value. Accordingly, the stiffness controller 117 varies the bending stiffness of the variable stiffness units 60 in the segments 14-2 and 14-4 (the stiffness control is turned ON). As a result, the segments 14-2 and 14-4 become more flexible and easier to bend in the directions indicated by arrows A2 and A1, respectively. Thereafter, at time T17, when the contact pressure at the point P12 on the posterior side of the segment 14-2 is less than the threshold value, or when the bending moment at the point P14 on the posterior side of the segment 14-4 is less than the threshold value, the stiffness controller 117 sets the bending stiffness of the variable stiffness units 60 provided in the segments 14-2 and 14-4 back to the original value (the stiffness control is turned OFF), respectively.

At time T18, as shown as D in the timeline of FIG. 28, the segment 14-2 of the flexible tube section 14 of the insertion section 11 has passed through the flexure 71, and the segment 14-3 on the posterior side is approaching the flexure 71. At this time, the segment 14-3 of the flexible tube section 14 is in contact with the flexure 71, so that the contact pressure P at the point P13 on the posterior side of the segment 14-3 is greater than or equal to the threshold value. In addition, the bending moment at the point P15 on the posterior side of the segment 14-5 is greater than or equal to the threshold value. Accordingly, the stiffness controller 117 varies the bending stiffness of the variable stiffness units 60 provided in the segments 14-3 and 14-5 (the stiffness control is turned ON). As a result, the segments 14-3 and 14-5 become more flexible and easier to bend in the directions indicated by arrows A2 and A1. Thereafter, at time T19, when the contact pressure at the point P13 on the posterior side of the segment 14-3 is less than the threshold value, or when the bending moment at the point P15 on the posterior side of the segment 14-5 is less than the threshold value, the stiffness controller 117 sets the bending stiffness of the variable stiffness units 60 in the segments 14-3 and 14-5 back to the original values (the stiffness control is turned OFF), respectively.

As described above, it may be configured that the base point determination section 116 determines the base point of the variation in bending stiffness based on the value of the bending moment, and further determines the base points of the variation in bending stiffness based on the value of the contact pressure, and the stiffness controller 117 causes the variable stiffness unit 60 to vary the bending stiffness of the segments of the flexible tube section 14 including these base points in units of segments. Also with such control, a propulsive force is sufficiently given to the insertion section 11, so that patient's pain caused by the insertion section 11 pushing the flexure 71 is alleviated. Thus, a flexible tube insertion device or an insertion control device with improved insertability by suitably varying the bending stiffness of the flexible tube section 14 can be provided.

In the above explanation, the embodiments of the present invention have been described with reference to the endoscope apparatus 1 equipped with a medical endoscope 10, but the present invention is not limited to the endoscope apparatus, includes a flexible tube insertion device having a flexible insertion section.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion device comprising:
a flexible tube segmented along an axial direction into two or more segments, the flexible tube being configured to be inserted into an insertion target;
a variable stiffness actuator configured to vary bending stiffness of each of the two or more segments of the flexible tube;
and
a controller comprising hardware, the controller being configured to:
acquire shape information of the flexible tube;
calculate a bending moment of the flexible tube in each of the two or more segments based on the shape information;
set a base point of variation in the bending stiffness to a segment of the two or more segments based on the calculated bending moment; and
cause the variable stiffness actuator corresponding to at least the segment of the two or more segments to vary the bending stiffness.

2. The flexible tube insertion device according to claim 1, wherein:
the segment of the two or more segments including a point at which the flexible tube has a larger bending moment than at a point in other segments of the two or more segments, and
the controller causes the variable stiffness actuator corresponding to at least the segment of the two or more segments to reduce the bending stiffness.

3. The flexible tube insertion device according to claim 2, wherein:
the segment of the two or more segments including a point in the flexible tube at which the bending moment indicates a local maximum value; and
the controller causes the variable stiffness actuator corresponding to at least the segment of the two or more segments to reduce the bending stiffness.

4. The flexible tube insertion device according to claim 1, wherein
the segment of the two or more segments including a point at which a distance from a virtual line is longer than a distance from the virtual line to a point in other segments of the two or more segments;
the controller causes the variable stiffness actuator corresponding to at least the segment of the two or more segments to reduce the bending stiffness, and
the virtual line being orthogonal to a tangent line to a shape of the flexible tube corresponding to a position of a bend in the insertion target, and the virtual line passing through the position of the bend in the insertion target.

5. The flexible tube insertion device according to claim 4, wherein the distance from the point on the segment of the two or more segments to the virtual vertical line is a maximum value as compared to the other segments of the two or more segments.

6. The flexible tube insertion device according to claim 1, wherein the controller is further configured to calculate a bending moment based on the shape information to calculate a position of a point at which the bending moment indicates a local maximum value.

7. The flexible tube insertion device according to claim 1, wherein the controller causes the variable stiffness actuator corresponding to the segment of the two or more segments to vary the bending stiffness of a base point peripheral portion including a point at which the bending moment indicates a local maximum value so that the bending stiffness is lower than an initial value.

8. The flexible tube insertion device according to claim 1, wherein the controller is further configured to determine a timing for varying the bending stiffness based on the shape information.

9. The flexible tube insertion device according to claim 8, wherein the controller is further configured to:
calculate a bending moment based on the shape information to calculate a position of a point at which the bending moment indicates a local maximum value, and
start the variation in the bending stiffness when the calculated bending moment is greater than or equal to a predetermined threshold value.

10. The flexible tube insertion device according to claim 9, wherein the controller stops the variation in the bending stiffness when the calculated bending moment is less than the predetermined threshold value.

11. The flexible tube insertion device according to claim 9, wherein the threshold value can be freely determined.

12. The flexible tube insertion device according to claim 8, further comprising:
a bendable section connected to the flexible tube at a distal end side of the flexible tube, the bendable section being configured to actively change a bent shape, and
at least one first force sensor arranged in the flexible tube and at least one second force sensor arranged the bendable section, the first and second force sensors being configured to detect an external force exerted on the flexible tube and on the bendable section, respectively; wherein
the controller starts the variation in the bending stiffness when a contact pressure exerted on the flexible tube and the bendable section is greater than or equal to a predetermined threshold value, based on contact pressure information of the flexible tube and the bendable section that is calculated based on information obtained by the first and second force sensors.

13. The flexible tube insertion device according to claim 12, wherein the controller stops the variation in the bending stiffness when the contact pressure exerted on the flexible tube and the bendable section is less than the predetermined threshold value, based on the contact pressure information of the flexible tube and the bendable section so that the controller stops varying the bending stiffness at the determined timing.

14. The flexible tube insertion device according to claim 12, wherein the threshold value can be freely determined.

15. The flexible tube insertion device according to claim 1, further comprising a bent shape sensor configured to measure a bent shape of the flexible tube and input the bent shape as the shape information to the controller.

16. An insertion control device for a flexible tube segmented along an axial direction into two or more segments, the flexible tube being configured to be inserted into an insertion target, the insertion control device comprising:
a controller comprising hardware, the controller being configured to:
acquire shape information of the flexible tube;
calculate a bending moment of the flexible tube in each of the two or more segments of the flexible tube based on the shape information;

set a base point of variation in a bending stiffness to a segment of the two or more segments based on the calculated bending moment; and cause a variable stiffness actuator corresponding to at least the segment of the two or more segments to vary the bending stiffness.

17. An insertion method of a flexible tube into an examination target, the flexible tube being segmented along an axial direction into two or more segments, the insertion method comprising:

inserting the flexible tube into the examination target;

acquiring shape information of the flexible tube;

calculating a bending moment of the flexible tube in each of the two or more segments of the flexible tube based on the shape information;

setting a base point of variation in a bending stiffness to a segment of the two or more segments based on the calculated bending moment; and varying a stiffness of at least the segment of the two or more segments.

* * * * *